(12) United States Patent
You et al.

(10) Patent No.: US 6,403,356 B1
(45) Date of Patent: Jun. 11, 2002

(54) MUTANT PENICILLIN G ACYLASES

(75) Inventors: Li You, Jamesville; John James Usher, East Syracuse; Brenda Joyce White, Jamesville, all of NY (US); Jiri Novotny, Princeton, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 08/962,281

(22) Filed: Oct. 31, 1997

Related U.S. Application Data

(60) Provisional application No. 60/030,365, filed on Nov. 5, 1996.

(51) Int. Cl.[7] ............................ C12N 9/84; C12N 15/55; C12N 15/70; C12N 15/11
(52) U.S. Cl. ................ 435/230; 435/69.1; 435/252.33; 435/320.1; 435/471; 435/45; 536/23.2
(58) Field of Search ................ 435/230, 69.1, 435/252.33, 320.1, 45, 471; 536/23.2

(56) References Cited

U.S. PATENT DOCUMENTS

| | | | | |
|---|---|---|---|---|
| 4,554,250 A | * | 11/1985 | McCullough | 435/320.1 |
| 4,774,179 A | | 9/1988 | Ichikawa et al. | 435/51 |
| 5,053,335 A | * | 10/1991 | Schumacher et al. | 435/230 |
| 5,168,048 A | | 12/1992 | Quax et al. | 435/230 |
| 5,192,678 A | | 3/1993 | Iwami et al. | 435/228 |
| 5,229,274 A | * | 7/1993 | Crawford et al. | 435/69.1 |
| 5,320,948 A | | 6/1994 | Iwami et al. | 435/47 |
| 5,336,613 A | | 8/1994 | Niwa et al. | 435/228 |
| 5,457,032 A | * | 10/1995 | Quax et al. | 345/43 |
| 5,516,679 A | | 5/1996 | Chiang et al. | 435/320 |
| 5,695,978 A | * | 12/1997 | Quax | 435/320 |
| 5,891,703 A | * | 4/1999 | Van Der Laan et al. | 435/230 |
| 5,935,831 A | | 8/1999 | Quax et al. | 435/471 |
| 6,033,823 A | | 3/2000 | VanDerLaan et al. | 435/230 |

FOREIGN PATENT DOCUMENTS

| | | |
|---|---|---|
| EP | 0283218 | 9/1988 |
| EP | 0322032 | 6/1989 |
| EP | 0 453 048 A1 | 4/1991 |
| EP | 0558241 | 4/1995 |
| EP | 718402 | 6/1996 |
| WO | WO9116435 | 10/1991 |
| WO | WO95/12680 | 5/1995 |
| WO | WO8600929 | 2/1996 |
| WO | WO 96/05318 | 2/1996 |
| WO | WO98/20120 | 5/1998 |

OTHER PUBLICATIONS

J Fei et al., Shiyan Shengwu Xuebao (Acta Biologiae Experimentals Sinica), 1992, vol. 25, pp. 289–293. (English Abstract at end of document).
J. Brannigan et al., Perspectives in Protein Engineering [Geisow, M. J., et al., Eds.; Mayflower Worldwide Pub.], 1995, pp. 124–125.
H. J. Duggleby et al., Nature, 1995, vol. 373, pp. 264–268.
Barbero et al., Gene, 1986, vol. 49, pp. 69–80.
Daumy, J. Bacteriol., 1985, vol. 163, pp. 1279–1281.
Meevootisom et al., Appl. Microbiol. Biotechnology, 1987, vol. 25, No. 4, pp. 372–378.
Joris et al., J. Biochem., 1985, vol. 250, pp. 313–324.
Matsuda et al., J. Bacteriol., 1987, vol. 169, pp. 5815–5820.

(List continued on next page.)

Primary Examiner—Ponnathapu Achutamurthy
Assistant Examiner—William W. Moore
(74) Attorney, Agent, or Firm—Audrey F. Sher; Christopher A. Klein; Michael P. Dougherty

(57) ABSTRACT

New mutant penicillin G acylases preferably from *E. coli* are provided, exhibiting altered enzymatic activity. These penicillin G acylases are obtained by expression of a gene encoding said penicillin G acylase having an amino acid sequence which differs at least in one amino acid from the wild-type penicillin G acylase.

24 Claims, 7 Drawing Sheets

---

1. METHIONINE A142 - ALA   TTT GTG GGC ACC <u>GCG</u> GCA AAC CGC TTC
   PHE VAL GLY THR <u>ALA</u> ALA ASN ARG PHE

2. PHE A146 - ALA   ATG GCA AAC CGC <u>TTC</u> TCT GAT AGC ACT
   MET ALA ASN ARG <u>ALA</u> SER ASP SER THR

3. PHE B24 - ALA/LEU/VAL/PRO/TYR/MET/SER/CYS/GLY/ASP/LYS/ARG/
   ILE/THR/GLN/ASN/GLU/TRP

AAT GGT CCG CAG <u>GCT</u> GGC TGG TAT GCG
   ASN GLY PRO GLN <u>ALA</u> GLY TRP TYR ALA
   ↓
   Other amino acid changes at B24 are :

<u>TTC</u> <u>TTG</u> <u>CCT</u> <u>TCT</u> <u>ATG</u> <u>CTC</u> <u>TGT</u> <u>GGT</u> <u>CAC</u> <u>TTT</u> <u>AGA</u>
   <u>LEU</u> <u>VAL</u> <u>PRO</u> <u>TYR</u> <u>MET</u> <u>SER</u> <u>CYS</u> <u>GLY</u> <u>HIST</u> <u>LYS</u> <u>ARG</u>

<u>ATT</u> <u>ACT</u> <u>CAA</u> <u>AAT</u> <u>GAA</u> <u>TGG</u>
   <u>ILE</u> <u>THR</u> <u>GLN</u> <u>ASN</u> <u>GLU</u> <u>TRP</u>

4. VALINE B56 - SER/THRE   TAT CCT GGG CTG <u>AGT</u> TTT GGT CAT AAT
   TYR PRO GLY LEU <u>SER</u> PHE GLY HIS ASN
   ↓
   <u>ACT</u>
   <u>THR</u>

5. ISOLEUCINE B177 - PHE   TAT CCT GGG CTG <u>TCT</u> TTT GGT CAT AAT
   GLN ALA CTG ACC <u>PHE</u> ASN TRP TYR TAT

OTHER PUBLICATIONS

Matsuda et al., J. Bacteriol., 1987, vol. 169, pp. 5821–5826.

Norrander et al., Gene, 1983, vol. 26, pp. 101–106.

Schumacher et al., Nucleic Acids Research, 1989, vol. 14, No. 14, pp. 5713–5727.

Stanssens et al., Nucleic Acids Research, 1986, vol. 12, pp. 4441–4454.

Forney et al., Applied & Environmental Microbiology, 1989, vol. 55, pp. 2550–2555.

Ishii et al., European Journal of Biochemistry, 1995, vol. 230, pp. 773–778.

Roa et al., Biochemical Journal, 1994, vol. 303, pp. 869–875.

Peng et al., Institute of Biophysics, Chinese Academy of Sciences, 1994, vol. 21, No. 2, pp. 155–160. (English Abstract attached).

Keilmann et al., Biological Chemistry, 1993, vol. 374,. No. 10, p. 983–992.

Prieto et al., Applied Microbiology and Biotechnology, 1992, vol. 36, No. 5, pp. 659–662.

Martin et al., Biochemical Journal, 1991, vol. 280, pp. 659–662.

D. Sizmann et al., European Journal of Biochemistry, 1990, vol. 192, pp. 143–151.

Deshpande et al., World Journal of Microbiology and Biotechnology, 1994, vol. 10, No. 2, pp. 129–138.

Williams et al., J.Cell Biochem. (1985)/Suppl. p. 99.

Prieto et al., Appl Microbiol Biotechnol. 33 (1990) 553–559.

Martin et al., Biochimica et Biophysica Acta 1037 (1990) 133–139.

Wang Min et al., Shiyan Shengwu Xuebao 24 (1991), 1, 51–54.

Kyeong Sook Choi et al., Journal of Bacteriology 174 (1992) 6270–6276.

Slade et al., Eur. J. Biochem. 197 (1991) 75–80.

Niersbach et al. Biotechnology Letters 17, 1, (1995) 19–24.

Gabriel del Rio et al., Biotechnology and Bioengineering 48 (1995) 141–148.

Niersbach et al. (1995) Appl. Microbiol. Bioetechnol. 43:4:679–684.

* cited by examiner

Alpha subunit

```
  1  GAG CAG TCG TCA AGT GAG ATA AAG ATT GTT CGC GAT GAA TAC
     Glu Gln Ser Ser Ser Glu Ile Lys Ile Val Arg Asp Glu Tyr

43  GGC ATG CCG CAT ATT TAT GCC AAT GAT ACA TGG CAC CTA TTT
     Gly Met Pro His Ile Tyr Ala Asn Asp Thr Trp His Leu Phe

85  TAT GGC TAT GGC TAT GTA GTA GCA CAA GAT CGC CTT TTT CAG
     Tyr Gly Tyr Gly Tyr Val Val Ala Gln Asp Arg Leu Phe Gln

127  ATG GAA ATG GCA CGT CGC AGT ACT CAA GGG ACT GTC GCG GAA
     Met Glu Met Ala Arg Arg Ser Thr Gln Gly Thr Val Ala Glu

169  GTG CTT GGC AAA GAT TTT GTG AAA TTT GAT AAA GAT ATC CGT
     Val Leu Gly Lys Asp Phe Val Lys Phe Asp Lys Asp Ile Arg

211  CGT AAC TAC TGG CCG GAT GCT ATC CGG GCG CAA ATT GCT GCC
     Arg Asn Tyr Trp Pro Asp Ala Ile Arg Ala Gln Ile Ala Ala

253  CTT TCC CCA GAG GAT ATG TCC ATT CTG CAA GGC TAC GCT GAT
     Leu Ser Pro Glu Asp Met Ser Ile Leu Gln Gly Tyr Ala Asp

295  GGA ATG AAT GCC TGG ACT GAT AAG GTA AAT ACC AAT CCA GAG
     Gly Met Asn Ala Trp Thr Asp Lys Val Asn Thr Asn Pro Glu

337  ACG CTC TTA CCA AAA CAG TTT AAT ACA TTT GGC TTT ACT CCT
     Thr Leu Leu Pro Lys Gln Phe Asn Thr Phe Gly Phe Thr Pro

379  AAG CGC TGG GAA CCG TTT GAT GTC GCG ATG ATA TTT GTG GGC
     Lys Arg Trp Glu Pro Phe Asp Val Ala Met Ile Phe Val Gly

421  ACC ATG GCA AAC CGC TTC TCT GAT AGC ACT AGC GAA ATT GAT
     Thr Met Ala Asn Arg Phe Ser Asp Ser Thr Ser Glu Ile Asp

463  AAT CTG GCA CTG CTA ACG GCT TTA AAA GAT AAA TAT GGT GTA
     Asn Leu Ala Leu Leu Thr Ala Leu Lys Asp Lys Tyr Gly Val

505  TCA CAA GGC ATG GCG GTA TTT AAT CAG TTG AAA TGG CTG GTA
     Ser Gln Gly Met Ala Val Phe Asn Gln Leu Lys Trp Leu Val

547  AAC CCA TCA GCG CCA ACC ACT ATT GCC GTA CAA GAG AGT AAC
     Asn Pro Ser Ala Pro Thr Thr Ile Ala Val Gln Glu Ser Asn

589  TAC CCA CTT AAA TTT AAT CAG CAA AAC TCG CAA ACA GCA
     Tyr Pro Leu Lys Phe Asn Gln Gln Asn Ser Gln Thr Ala
```

FIG. 1A

Beta subunit

```
  1  AGC AAT ATG TGG GTG ATC GGC AAA AGC AAA GCC CAG GAT GCG
     Ser Asn Met Trp Val Ile Gly Lys Ser Lys Ala Gln Asp Ala

43  AAA GCA ATC ATG GTA AAT GGT CCG CAG TTT GGC TGG TAT GCG
     Lys Ala Ile Met Val Asn Gly Pro Gln Phe Gly Trp Tyr Ala

85  CCT GCG TAT ACT TAT GGT ATT GGT CTG CAC GGT GCT GGT TAT
     Pro Ala Tyr Thr Tyr Gly Ile Gly Leu His Gly Ala Gly Tyr

127  GAT GTC ACT GGC AAT ACA CCA TTT GCC TAT CCT GGG CTG GTT
     Asp Val Thr Gly Asn Thr Pro Phe Ala Tyr Pro Gly Leu Val

169  TTT GGT CAT AAT GGT GTG ATT TCC TGG GGA TCA ACG GCA GGT
     Phe Gly His Asn Gly Val Ile Ser Trp Gly Ser Thr Ala Gly

211  TTC GGC GAT GAT GTC GAT ATT TTT GCT GAA CGG CTG TCG GCA
     Phe Gly Asp Asp Val Asp Ile Phe Ala Glu Arg Leu Ser Ala

253  GAG AAA CCA GGC TAC TAC TTG CAT AAT GGT AAG TGG GTG AAA
     Glu Lys Pro Gly Tyr Tyr Leu His Asn Gly Lys Trp Val Lys

295  ATG TTA AGC CGT GAG GAA ACC ATT ACG GTG AAA AAT GGT CAG
     Met Leu Ser Arg Glu Glu Thr Ile Thr Val Lys Asn Gly Gln

337  GCA GAG ACC TTT ACT GTC TGG CGT ACG GTG CAT GGC AAC ATT
     Ala Glu Thr Phe Thr Val Trp Arg Thr Val His Gly Asn Ile

379  CTC CAA ACT GAC CAG ACG ACA CAA ACG GCT TAC GCT AAA TCC
     Leu Gln Thr Asp Gln Thr Thr Gln Thr Ala Tyr Ala Lys Ser

421  CGC GCA TGG GAT GGT AAA GAG GTG GCG TCT TTG CTG GCC TGG
     Arg Ala Trp Asp Gly Lys Glu Val Ala Ser Leu Leu Ala Trp

463  ACT CAT CAG ATG AAG GCC AAA AAT TGG CAG GAG TGG ACA CAG
     Thr His Gln Met Lys Ala Lys Asn Trp Gln Glu Trp Thr Gln

505  CAG GCA GCG AAA CAA GCA CTG ACC ATC AAC TGG TAC TAT GCT
     Gln Ala Ala Lys Gln Ala Leu Thr Ile Asn Trp Tyr Tyr Ala

547  GAT GTA AAC GGC AAT ATT GGT TAT GTT CAT ACT GGT GCT TAT
     Asp Val Asn Gly Asn Ile Gly Tyr Val His Thr Gly Ala Tyr

589  CCA GAT CGT CAA TCA GGC CAT GAT CCG CGA TTA CCC GTT CCT
     Pro Asp Arg Gln Ser Gly His Asp Pro Arg Leu Pro Val Pro

631  GGT ACG GGA AAA TGG GAC TGG AAA GGG CTA TTG CCT TTT GAA
     Gly Thr Gly Lys Trp Asp Trp Lys Gly Leu Leu Pro Phe Glu

673  ATG AAC CCT AAG GTG TAT AAC CCC CAG TCG GGA TAT ATT GCT
     Met Asn Pro Lys Val Tyr Asn Pro Gln Ser Gly Tyr Ile Ala

715  AAC TGG AAC AAT TCT CCC CAA AAA GAT TAT CCC GCT TCA GAT
     Asn Trp Asn Asn Ser Pro Gln Lys Asp Tyr Pro Ala Ser Asp
```

FIG. 1B

```
757   CTG TTT GCC TTT TTG TGG GGT GGT GCA GAT CGC GTT ACG GAG
      Leu Phe Ala Phe Leu Trp Gly Gly Ala Asp Arg Val Thr Glu

799   ATC GAC CGA CTG CTT GAG CAA AAG CCA CGC TTA ACT GCT GAT
      Ile Asp Arg Leu Leu Glu Gln Lys Pro Arg Leu Thr Ala Asp

841   CAG GCA TGG GAT GTT ATT CGC CAA ACC AGT CGT CAG GAT CTT
      Gln Ala Trp Asp Val Ile Arg Gln Thr Ser Arg Gln Asp Leu

883   AAC CTG AGG CTT TTT TTA CCT ACT CTG CAA GCA GCG ACA TCT
      Asn Leu Arg Leu Phe Leu Pro Thr Leu Gln Ala Ala Thr Ser

925   GGT TTG ACA CAG AGC GAT CCG CGT CGT CAG TTG GTA GAA ACA
      Gly Leu Thr Gln Ser Asp Pro Arg Arg Gln Leu Val Glu Thr

967   TTA ACA CGT TGG GAT GGC ATC AAT TTG CTT AAT GAT GAT GGT
      Leu Thr Arg Trp Asp Gly Ile Asn Leu Leu Asn Asp Asp Gly

1009  AAA ACC TGG CAG CAG CCA CCG TCT GCC ATC CTG AAC GTT TGG
      Lys Thr Trp Gln Gln Pro Pro Ser Ala Ile Leu Asn Val Trp

1051  CTG ACC AGT ATG TTG AAG CGT ACC GTA GTG GCT GCC GTA CCT
      Leu Thr Ser Met Leu Lys Arg Thr Val Val Ala Ala Val Pro

1093  ATG CCA TTT GAT AAG TGG TAC AGC GCC AGT GGC TAC GAA ACA
      Met Pro Phe Asp Lys Trp Tyr Ser Ala Ser Gly Tyr Glu Thr

1135  ACC CAG GAC GGC CCA ACT GGT TCG CTG AAT ATA AGT GTT GGA
      Thr Gln Asp Gly Pro Thr Gly Ser Leu Asn Ile Ser Val Gly

1177  GCA AAA ATT TTG TAT GAG GCG GTG CAG GGA GAC AAA TCA CCA
      Ala Lys Ile Leu Tyr Glu Ala Val Gln Gly Asp Lys Ser Pro

1219  ATC CCA CAG GCG GTT GAT CTG TTT GCT GGG AAA CCA CAG CAG
      Ile Pro Gln Ala Val Asp Leu Phe Ala Gly Lys Pro Gln Gln

1261  GAG GTT GTG TTG GCT GCG CTG GAA GAT ACC TGG GAG ACT CTT
      Glu Val Val Leu Ala Ala Leu Glu Asp Thr Trp Glu Thr Leu

1303  TCC AAA CGC TAT GGC AAT AAT GTG AGT AAC TGG AAA ACA CCT
      Ser Lys Arg Tyr Gly Asn Asn Val Ser Asn Trp Lys Thr Pro
```

FIG. 1C

| | | | | | | | | | | | | |
|---|---|---|---|---|---|---|---|---|---|---|---|---|
|1345|GCA|ATG|GCC|TTA|ACG|TTC|CGG|GCA|AAT|AAT|TTC|TTT|GGT|GTA|
| |Ala|Met|Ala|Leu|Thr|Phe|Arg|Ala|Asn|Asn|Phe|Phe|Gly|Val|
|1387|CCG|CAG|GCC|GCA|GCG|GAA|GAA|ACG|CGT|CAT|CAG|GCG|GAG|TAT|
| |Pro|Gln|Ala|Ala|Ala|Glu|Glu|Thr|Arg|His|Gln|Ala|Glu|Tyr|
|1429|CAA|AAC|CGT|GGA|ACA|GAA|AAC|GAT|ATG|ATT|GTT|TTC|TCA|CCA|
| |Gln|Asn|Arg|Gly|Thr|Glu|Asn|Asp|Met|Ile|Val|Phe|Ser|Pro|
|1471|ACG|ACA|AGC|GAT|CGT|CCT|GTG|CTT|GCC|TGG|GAT|GTG|GTC|GCA|
| |Thr|Thr|Ser|Asp|Arg|Pro|Val|Leu|Ala|Trp|Asp|Val|Val|Ala|
|1513|CCC|GGT|CAG|AGT|GGG|TTT|ATT|GCT|CCC|GAT|GGA|ACA|GTT|GAT|
| |Pro|Gly|Gln|Ser|Gly|Phe|Ile|Ala|Pro|Asp|Gly|Thr|Val|Asp|
|1555|AAG|CAC|TAT|GAA|GAT|CAG|CTG|AAA|ATG|TAC|GAA|AAT|TTT|GGC|
| |Lys|His|Tyr|Glu|Asp|Gln|Leu|Lys|Met|Tyr|Glu|Asn|Phe|Gly|
|1597|CGT|AAG|TCG|CTC|TGG|TTA|ACG|AAG|CAG|GAT|GTG|GAG|GCG|CAT|
| |Arg|Lys|Ser|Leu|Trp|Leu|Thr|Lys|Gln|Asp|Val|Glu|Ala|His|
|1639|AAG|GAG|TCG|CAG|GAA|GTG|TTG|CAC|GTT|CAG|AGA|TAA| | |
| |Lys|Glu|Ser|Gln|Glu|Val|Leu|His|Val|Gln|Arg|---| | |

FIG. 1D

1. METHIONINE A142 - ALA   TTT GTG GGC ACC GCG GCA AAC CGC TTC
                            PHE VAL GLY THR ALA ALA ASN ARG PHE

2. PHE A146 - ALA           ATG GCA AAC CGC TTC TCT GAT AGC ACT
                            MET ALA ASN ARG ALA SER ASP SER THR

3. PHE B24 - ALA/LEU/VAL/PRO/TYR/MET/SER/CYS/GLY/ASP/LYS/ARG/
   ILE/THR/GLN/ASN/GLU/TRP

AAT GGT CCG CAG GCT GGC TGG TAT GCG
   ASN GLY PRO GLN ALA GLY TRP TYR ALA
                     |
   Other amino acid changes at B24 are :

| TTC | TTG | CCT | TCT | ATG | CTC | TGT | GGT | CAC | TTT | AGA |
   |-----|-----|-----|-----|-----|-----|-----|-----|-----|-----|-----|
   | LEU | VAL | PRO | TYR | MET | SER | CYS | GLY | HIST| LYS | ARG |

| ATT | ACT | CAA | AAT | GAA | TGG |
   |-----|-----|-----|-----|-----|-----|
   | ILE | THR | GLN | ASN | GLU | TRP |

4. VALINE B56 - SER/THRE    TAT CCT GGG CTG AGT TTT GGT CAT AAT
                            TYR PRO GLY LEU SER PHE GLY HIS ASN
                                             |
                                            ACT
                                            THR

5. ISOLEUCINE B177- PHE     TAT CCT GGG CTG TCT TTT GGT CAT AAT
                            GLN ALA CTG ACC PHE ASN TRP TYR TAT

FIG. 2

MUTANT PENICILLIN G ACYLASES

CROSS-REFERENCE TO RELATED APPLICATIONS

This application claims the benefit of U.S. Provisional Application No. 60/030,365, filed Nov. 5, 1996.

FIELD OF THE INVENTION

The present invention relates to mutated genes encoding Type II penicillin G acylases, to penicillin G acylases encoded by these genes resulting in altered properties, and to methods for the synthesis of β-lactam antibiotics using these penicillin G acylases.

BACKGROUND OF THE INVENTION

Today, semisynthetic β-lactam derivatives such as ampicillin, amoxicillin, cephalexin, cefadroxil, and cefprozil are, on an industrial scale, prepared by chemical methods. The synthesis of these antibiotics catalyzed by enzymes constitutes a clear example of an enzymatic reaction of possible industrial importance. The enzymatic approach has several advantages as compared to conventional chemical methods: (1) avoidance of toxic reagents and solvents; (2) enzyme specificity renders protection of carboxyl groups in the antibiotic nucleus unnecessary; (3) avoidance of side reactions, including racemization.

In this context, penicillin G acylase offers a great advantage. Penicillin G acylase, also called penicillin G amidase or benzylpenicillin amidohydrolase [EC. 3.5.1.11], refers to a group of hydrolases from microorganisms, especially bacteria, capable of hydrolyzing the 6 acyl group of penicillins or the 7 acyl group of cephalosporins having the general structures of I and II to their corresponding free amine forms (6-APA and its derivatives, 3.5 III, and 7-ACA and its derivatives, IV).

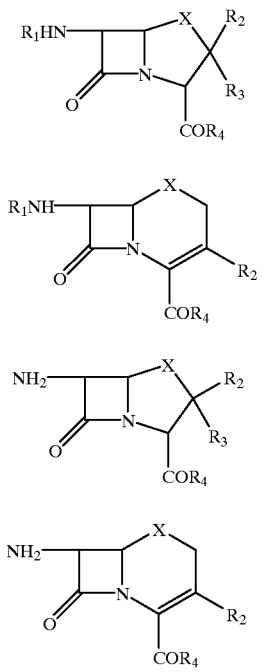

wherein
R1=phenylacetyl, phenoxyacetyl, hydroxyphenylglycine, phenylglycine and their derivatives, acetyl, adipyl and their derivatives R2, R3=aliphatic or aromatic entities with or without one or more O, S, N atoms R4=aliphatic or aromatic alcohols and their derivatives with or without one or more O. S. N atoms The preferred acyl group is phenylacetyl, although other aromatic and aliphatic (hydrophobic, or charged/polar) acyl groups can also be hydrolyzed to varying degrees (generally less). The preference for different acyl groups are not necessarily true for the reverse reaction, namely the formation of amide bonds between the acyl groups and 6-APA and 7-ACA (III and IV). For instance, the chloroacetyl group can be put on to 7-ACA much faster than most aromatic acyl groups (patent JP08000284-A). For many currently marketed β-lactam antibiotics, the acyl groups are aromatic functions with varying degrees of hydrophobicity. The wild type penicillin G amidase can catalyze the semisyntheses (amide bond formation) of these antibiotics, but the reactions rarely go to completion under suitable or economical conditions for the production of these antibiotics. Improvements in the production yield and efficiency of these reactions are highly desired.

There are many reports in the literature of penicillin G acylases which contain altered amino acid residues exhibiting altered substrate specificity or changes in catalytic activity. Prieto et al. (I. Prieto et al., Appl. Microbiol. Biotechnol.33 (1990) 553–559) replaced Met168 in penicillin G acylase from *K. citrophila* with Ala, Asp, Val, Asn, and Tyr resulting in modified kinetic parameters for penicillin G and penicillin V deacylation; the substitution of Asn with Lys375 or Tyr with His481 did not. Martin et al. (J. Martin & I. Prieto, Biochimica et Biophysica Acta 1037 (1990) 133–139) describe a mutant of penicillin G acylase with different substrate specificity and enhanced thermal stability when Met168 was changed to Ala. Wang Min et al. (Wang Min et al. Shiyan Shengwu Xuebao 24 (1991), 1, 51–54) reported the replacement of Ser177 in *E. coli* penicillin G acylase with Gly, Thr, Leu, Arg, all of which changes resulted in inactive enzymes. Kyeong Sook et al. (Kyeong Sook et al. Journal of Bacteriology 174 (1992) 6270–6276) and Slade et al. (Slade et al. Eur.J. Biochem. 197 (1991) 75–80) have demonstrated Ser290 to be an essential amino acid residue of penicillin G acylase from *E. coli*. Substitution of Ser290 with Cys completely inactivated the enzyme. Niersbach et al. (Niersbach et al. Biotechnology Letters 17, 1, (1995) 19–24) replaced Gly359 with aspartic acid in penicillin G acylase from *E. coli*. The mutant enzyme lost the ability to hydrolyze penicillin G but exhibited the novel ability to hydrolyze phthalyl-L-leucine and phthalyl-glycyl-L-proline. An enhanced stability at alkaline pH was demonstrated by a site-directed mutant of penicillin G acylase from *E. coli* when Trp431 was changed to Arg (Gabriel del Rio et al. Biotechnology and Bioengineering 48 (1995) 141–148).

The inventors herein present mutant penicillin G acylases having altered enzymatic activities when compared with the wild type enzyme.

SUMMARY OF THE INVENTION

In one aspect of the invention the DNA sequence of the Type II wild-type penicillin G acylase, preferably from prokaryotic organisms (the structure of the enzyme from *E. coli* is given in FIGS. 1A through 1D), is altered to encode mutant penicillin G acylases. Type II acylases all share a common molecular structure. Type II acylases are heterodimers composed of a small subunit (alpha; 16–26 kilodaltons (kDa)) and a large subunit (beta; 54–66 kDa). As used herein the term "penicillin G acylase" is intended to mean prokaryotic Type II acylase as well as its preenzyme and preproenzyme forms. The DNA sequence (SEQ.ID.NO.:1) and corresponding amino acid sequence (SEQ.ID.NO.:2) for the alpha subunit of the wild type penicillin G acylase from *E. coli* are shown in FIG. 1A. The DNA sequence (SEQ.ID.NO.:3) and corresponding amino acid sequence (SEQ.ID.NO.:4) for the beta subunit of the wild type penicillin G acylase from *E. coli* are shown in FIGS. 1B through 1D. In accordance with the present invention, one or more selected amino acid residues are substituted with different amino acid residues from the group of natural amino acids. Of course, in the mutated DNA sequences of the invention corresponding changes in the DNA sequence are made in order to encode the desired amino acid(s) at the desired position(s). The structural changes were determined based on the X-ray crystallographic structure of the wild-type penicillin G acylase. The DNA and amino acid sequence changes for each substitution in accordance with the present invention are shown in FIG. 2.

In accordance with the invention the following substitutions at one or more of the designated sites are provided:
1. On the Alpha Subunit:
   DNA basepairs:A424–426 (MetA142—Ala)
   DNA basepairs:A436–438 (PheA146—Ala)
2. On the Beta Subunit:
   DNA basepairs:B70–72 (PheB24—Ala, Leu, Val, Pro, Tyr, Met, Ser, Cys, Gly, Asp, Lys, Arg, Typ, Thr, Ile, Glu, Gln, Asn or His).
   DNA basepairs:B166–168 (ValB56—Ser or Thr)
   DNA basepairs: B529–531 (IleB177—Phe)

In the nomenclature used above, "A" represents the alpha subunit, "B" represents the beta subunit; the numbered positions are conventional amino terminus to carboxy terminus for amino acid sequences, and 5' to 3' for DNA sequences; the amino acid preceding the amino acid position number represents the wild type amino acid and the amino acid following the amino acid position number represents the substitute amino acid, for example, "ValB56—Ser or Thr" means that amino acid at position 56 in the wild type beta subunit is valine which is substituted with either serine or threonine to make a mutant acylase of the invention.

The altered acylases of the invention have altered enzymatic activities when compared with the corresponding wild-type penicillin G acylase.

The most preferred altered (mutant) penicillin G acylase has a single amino acid alteration (PheB24-Ala), and is capable of synthesizing β-lactam antibiotics with significantly higher yield and efficiency than the wild type enzyme.

In other aspects the present invention is also directed to vectors which comprise the altered nucleic acid sequences of the invention, and microorganism host cells transformed with said vectors. The invention also concerns processes for production of the altered acylases comprising culturing the host cells of the invention, preferably followed by isolation of the acylase.

In yet another aspect the invention provides methods to use the said mutant penicillin G acylase for the semisyntheses of β-lactam antibiotics (e.g., cefadroxil, cefprozil, amoxicillin). Conditions, such as substrate concentrations, pH values and temperatures, are presented hereinafter. The yields and efficiencies of the semisynthetic reactions using the mutant penicillin G acylases are preferably improved when compared with the wild type enzyme.

BRIEF DESCRIPTION OF THE DRAWINGS

FIG. 1A: Nucleotide (DNA) sequence of alpha subunit of the *E. coli* wild-type penicillin G amidase gene and the corresponding amino acid sequence encoded by the nucleotide sequence.

FIG. 1B: Nucleotide (DNA) sequence of beta subunit of the *E. coli* wild-type penicillin G amidase gene and the corresponding amino acid sequence encoded by the nucleotide sequence.

FIG. 1C: continuation of FIG. 1B.

FIG. 1D: continuation of FIG. 1C.

FIG. 2: DNA and amino acid sequences of the relevant fragments of penicillin G acylase illustrating the exact sites of mutations in accordance with the invention. DNA fragment 1 is SEQ.ID.NO.:5, amino acid fragment 1 is SEQ.ID.NO.:6, DNA fragment 2 is SEQ.ID.NO.:7, amino acid fragment 2 is SEQ.ID.NO.:8, DNA fragment 3 is SEQ.ID.NO.:9, amino acid fragment 3 is SEQ.ID.NO.:10, DNA fragment 4 is SEQ.ID.NO.:11, amino acid fragment 4 is SEQ.ID.NO.:12, and DNA fragment 5 is SEQ.ID.NO.:13, amino acid fragment 5 is SEQ.ID.NO.:14.

DETAILED DESCRIPTION OF THE INVENTION

Figure 3:
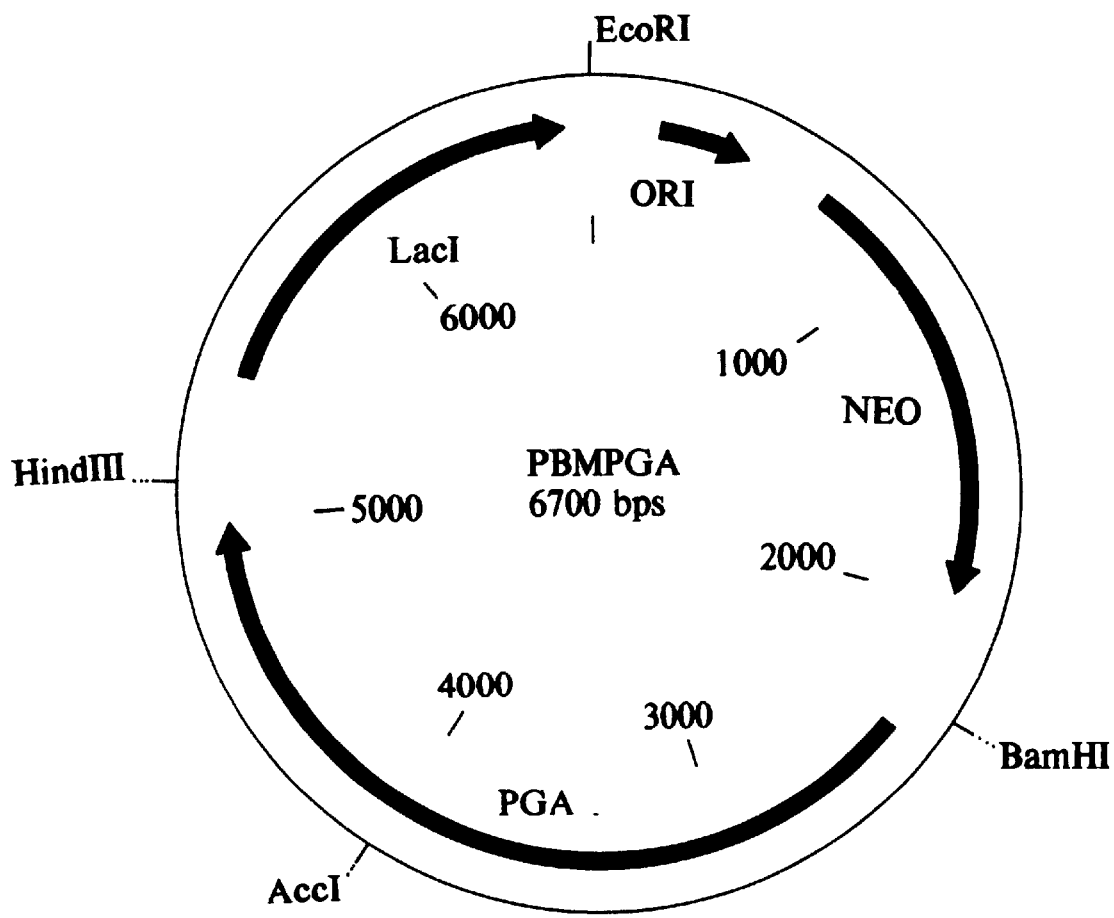
FIG. 3: Illustration of PBM vector referred to in Example 1 containing mutated DNA sequences of penicillin G acylases
Figure 4:
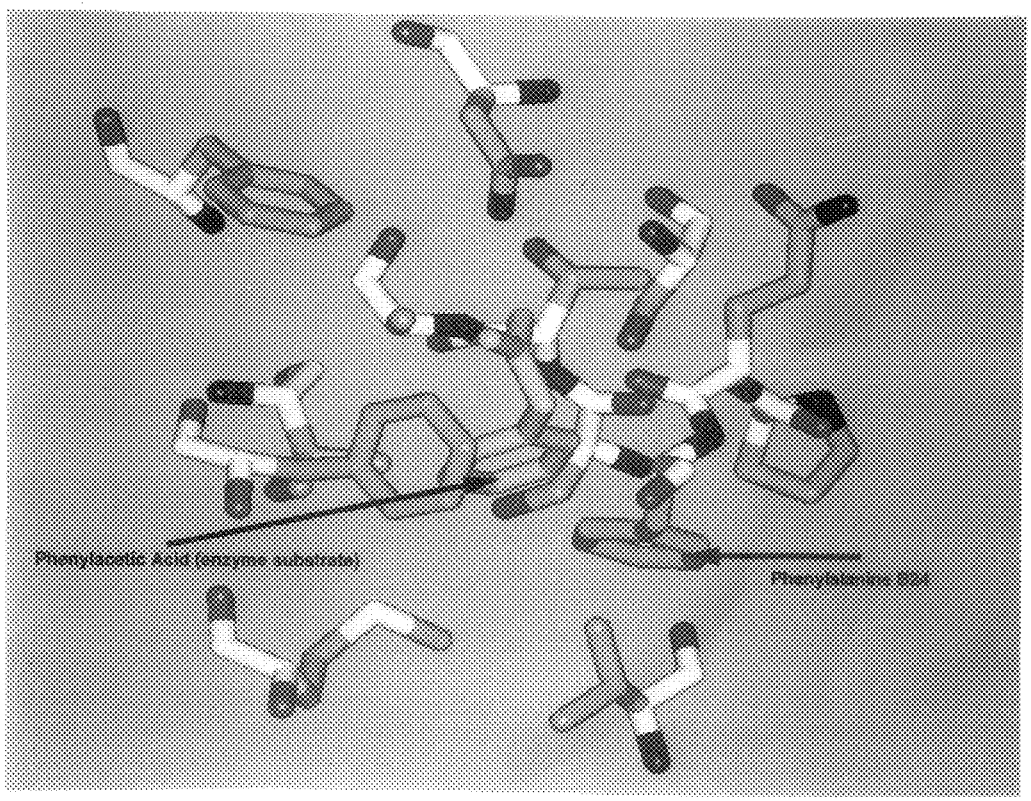
FIG. 4: Computer graphics image of the structure of the penicillin G acylase substrate binding site. For clarity, protein backbone trace is not shown. The isolated amino acids constituting the site are shown as stick structural diagrams. Atom types are coded by different shades of gray, i.e., polypeptide backbone carbons, white; side chain carbons, light gray; nitrogens, dark gray; oxygens, black. The cleaved substrate, phenylacetic acid, is marked by an arrow at the center of the site. The phenylalanine side chain B24 is also labeled with an arrow. As can be seen, the aromatic side chain ring of the B24 residue occupies an important position central to the site, in contact with the substrate, and shielding the substrate from solvent. The image was prepared from the X-ray crystallographic coordinates of the phenylacetic acid—penicillin G acylase complex.

The penicillin G acylases which are the subject of this invention have altered substrate specificity and/or altered specific activity when compared with the wild type enzyme. The enzymes of the invention preferably exhibit enhanced yield and/or efficiency when compared with the wild type enzyme. It is possible that routine experimentation may be required to determine optimal conditions for use of the altered enzymes of the invention. The wild type enzyme utilized herein to prepare the altered enzymes of the invention is obtained from prokaryotes such as *Escherichia coli, Kluyvera citrophila, Providencia rettgeri, Pseudomonas sp., Alcaligenes faecalis, Bacillus megaterium, Arthrobacter viscosus*, and the like. The acylase preferably has the following characteristics: (1) is isolated from the prokaryote *E. coli* (e.g., ATCC 11105) (2) is translated as a single peptide chain precursor (3) is processed after translation resulting in a heterodimer with a small N-terminal domain (the alpha subunit) and a larger C-terminal domain (the beta subunit). The molecular weight of the preferred alpha subunit is about 24000 and the molecular weight of the preferred beta subunit is about 62000. The active form of the preferred enzyme is typically found in the periplasmic of *E. coli*.

Current LC-MS data suggest that during post-translational processing in *E. coli* the alpha subunit is truncated at the C-terminus by about 10 to 15 amino acids, most likely by 12 or 13 amino acids. Similarly, the same data indicate that during post-translational processing the alpha subunit is truncated at the N-terminus by 1 or 2 amino acids. Thus, the present invention includes mutant penicillin G acylases wherein the alpha subunit has been truncated at the N-terminus by 1 or 2 amino acids and/or wherein said alpha subunit has been truncated at the C-terminus by 10 to 15 amino acids, preferably by 12 or 13 amino acids.

The alteration of the substrate specificity of penicillin G acylases is achieved in such a way that the mutant enzymes are able to cleave or synthesize penicillin and cephalosporin derivatives posessing side chains other than phenyacetyl, which is the natural side chain of penicillin G. Examples of side chains which are presently not significantly affected by penicillin G acylases are acyl groups derived from the dicarboxylic acids succinic acid, glutaric acid, adipic acid, aminoadipic acid, and the like.

The mutated enzymes of the invention may exhibit increased sterospecificity which can result in improved enantiomeric excess in conversion with racemic mixtures of chiral compounds. Such a property might make the acylases very useful for synthesis of enantiomerically pure semisynthetic antibiotics from racemic mixtures of phenyl acetyl side chains or activated derivatives of the phenlyacetyl side chains (e.g., phenylglycine-amides or esters therefrom, p-hydroxyphenylglycine-amides or esters therefrom, and the like) containing a chiral alpha carbon due to the presence of an amino group (e.g., as in, for example, ampicillin, cefalexin, amoxicillin, cefadroful cefaclor) or a hydroxyl group (as in, for example cefamandole).

The present invention also relates to the identification of penicillin G acylase mutants derived from wild-type enzyme via recombinant DNA methodology known in the art substituting one amino acid residue for a new residue. Mutants were analyzed for both hydrolytic and synthetic activity. Penicillin G acylase variants are preferred in which the transferase activity is improved with respect to the hydrolase activity. This makes the enzyme more useful in synthetic conversions. Mutants with improved performance in the enzymatic synthesis of antibiotics such as amoxicillin, cefadroxil, cefprozil, and cephalexin are preferred.

The introduction of a mutation in determined sites of a gene can be carried out by modification of a defined site of a DNA sequence using synthetic oligonucleotides. Mutants of penicillin G acylase in the present invention can be prepared by a process which comprises:

(1) introducing a mutation in specific sites of the gene encoding penicillin G acylase by standard polymerase chain reaction site-directed mutagenesis. Specific oligodeoxynucleotides for these mutations were synthesized by a commercial source. The oligonucleotides are homologous to the sequence to be mutagenized except for an internal portion which determines the mutation.

(2) cloning the mutagenized gene in a cloning vector.

(3) transforming a host strain with the recombinant vector.

(4) cultivating the host strain on a suitable culture medium.

(5) separating and immobilizing the mutant penicillin G acylase thus obtained.

(6) assaying the mutants with regard to hydrolytic and synthetic activity.

The mutagenesis of penicillin G acylase in accordance herein introduces new substrate specificity and/or altered enzymatic activity. To introduce point mutations, a rational approach is taken, relying on protein crystallography, molecular modeling, molecular biology, and protein chemistry techniques. According to the present invention, specific amino acid positions have been identified as important positions with regard to the catalytic properties of the enzyme. These residues include MetA142, PheA146, PheB24, ValB56, and IleB177. The identification of these residues is based on X-ray crystallographic structure.

To compare the enzymes of the invention with the wild type enzyme, the mutant and the wild type penicillin G acylases are in the form of crude cell lysates or immobilized solids, preferably the latter. The enzyme of the invention having mutation PheB24—Ala demonstrates an improved synthesis activity for β-lactam antibiotics and is therefore preferred.

The present invention also includes an expression vector comprising a nucleic acid sequence of the invention operably linked to a promoter sequence capable of directing its expression in a host cell. Preferred vectors are plasmids such as plasmid PBMPGA shown in FIG. 3. Expression vectors useful in the present invention typically contain an origin of replication, a promoter located in front (i.e., upstream of) the DNA sequence and followed by the DNA sequence coding for all or part of the mutant acylase. The DNA sequence coding for all or part of the mutant acylase is followed by transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and sequences which provide sites for cleavage by restriction endonucleases. The characteristics of the actual expression vector used must be compatible with the host cell which is to be employed. For example, when cloning in an *E. coli* cell system, the expression vector should contain promoters isolated from the genome of *E. coli* cells (e.g., tac, lac, and trp). Suitable origins of replication in *E. coli* various hosts include, for example, a ColEI plasmid replication origin. Suitable promoters include, for example, the tac, lac, and trp and the neo-r gene promoter from *E. coli*. Suitable termination sequences include, for example, the penicillin G acylase, T7 phage gene 10, and the neo-r gene terminators from *E. coli*. It is also preferred that the expression vector include a sequence coding for a selectable marker. The selectable marker is preferably antibiotic resistance. As selectable markers, ampicillin resistance, and neomycin resistance can be conveniently employed. All of these materials are known in the art and are commercially available.

Suitable expression vectors containing the desired coding and control sequences may be constructed using standard recombinant DNA techniques known in the art, many of which are described in Sambrook et al. Molecular Cloning: A Laboratory Manual, 2nd edition, Cold Spring Harbor Laboratory, Cold Spring Harbor, N.Y. (1989).

The present invention additionally concerns host cells containing an expression vector which comprises a DNA sequence coding for all or part of the mutant acylase. The host cells preferably contain an expression vector which comprises all or part of one of the DNA sequences having one or more mutations shown in FIG. 2. Further preferred are host cells containing an expression vector comprising one or more regulatory DNA sequences capable of directing the replication and/or the expression of, and operatively linked to a DNA sequence coding for, all or part of mutant acylase. Suitable host cells include, for example, *E. coli* HB101 (ATCC 33694) available from Life Technologies, Inc., P.O. Box 6009, Gaithersburg, Md. 20897; BL21 available from Novagen, Inc., 597 Science Drive, Madison, Wis. 53711; and the like.

Expression vectors may be introduced into host cells by various methods known in the art. For example, transfection of host cells with expression vectors can be carried out by the polyethylene glycol mediated protoplast transformation method. However, other methods for introducing expression vectors into host cells, for example, electroporation, biolistic injection, or protoplast fusion, can also be employed.

Once an expression vector has been introduced into an appropriate host cell, the host cell may be cultured under conditions permitting expression of the desired mutant acylase.

A host cell, *E. coli* BL21, containing plasmid pBMPGA ((pBMF1PGA)+) was deposited with the American Type Culture Collection, Rockville, Md. 20852, under the provisions of the Budapest Treaty on Sep. 4, 1997 and has the designation ATCC 98537.

Host cells containing an expression vector which contains a DNA sequence coding for all or part of the mutant acylase may be identified by one or more of the following five general approaches: (a) DNA-DNA hybridization; (b) the presence or absence of marker gene functions; (c) assessment of the level of transcription as measured by the production of penicillin G acylase mRNA transcripts in the host cell; (d) detection of the gene product immunologically; and (e) enzyme assay (calorimetric detection, etc.).

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

All amino acid residues identified herein are in the natural L-configuration. In keeping with standard polypeptide nomenclature, J. Biol. Chem. 243, 3557–3559 (1969), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |

-continued

TABLE OF CORRESPONDENCE

| SYMBOL | | |
|---|---|---|
| 1-Letter | 3-Letter | AMINO ACID |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

The polypeptides of the present invention may be obtained by synthetic means, i.e. chemical synthesis of the polypeptide from its component amino acids, by methods known to those of ordinary skill in the art. For example, the solid phase procedure described in Houghton et al., Proc. Natl. Acad. Sci. 82, 5131–5135 (1985) may be employed. It is preferred that the polypeptides be obtained by production in prokaryotic host cells expressing a DNA sequence coding for the mutant acylase, or by in vitro translation of the mRNA encoded by a DNA sequence coding for the mutant acylase. For example, the DNA sequence may be synthesized using PCR as described above and inserted into a suitable expression vector, which in turn may be used to transform a suitable host cell. The recombinant host cell may then be cultured to produce enzyme. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

The polypeptides of the present invention have been defined by means of determined DNA and deduced amino acid sequencing. Due to the degeneracy nature of the genetic code, which results from there being more than one codon for most of the amino acid residues and stop signals, other DNA sequences which encode the same amino acid sequence as depicted in FIG. 1 may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substituents such as methionine, N-formylmethionine used as leader sequences. All such variations are included within the scope of the present invention.

The invention also contemplates a process for producing a mutant penicillin G acylase of the invention comprising culturing a host cell of the invention under conditions suitable for production of the mutant acylase of the invention. For bacterial host cells, typical culture conditions are liquid medium containing the appropriate antibiotic and induction agent. Cultures are shaken or stirred at a temperature suitable for optimal production of enzyme, e.g., about 28° C. to about 29° C. Typical appropriate antibiotics include kanamycin, chloroamphenicol, tetrocyclin and the like. Typical induction agents include IPTG, lactose and the like.

The present invention also includes a process for producing a semi-synthetic 6-acylated penicillanic acid, a 7-acylated cephalosporanic acid or a salt or ester thereof which comprises contacting a corresponding 6-amino β-lactam or 7-ACA or salt or ester thereof, respectively, and an acylating agent with a mutant acylase of the invention under conditions suitable for acylation to occur. Typical acylating agents include esters or amides of the sidechains of amoxicillin, cefadroxil, cefprozil, etc. Typical acylating agents include, but are not limited to, phenylglycine, parahydroxyphenylglycine, phenylacetic acid, phenoxyacetic acid, their esters or amides. The preferred form of acylating agent is the ester of the above mentioned acids. The alcohol portion of these esters including, but are not limited to, methanol and its longer-chain analogues and their stereoisomers, ethylene glycol and its longer-chain analogues and their stereoisomers. Most preferred are ethylene glycol esters. Typical acylating conditions are in aqueous buffer at neutral pH or below, with constant stirring. A typical temperature is about 0° C. to about 35° C. The mutant acylase for use in the above process can be made in situ by the host cells or can be pre-made by the host cells. If cell-free mutant acylase is used, it can be in a crude cell lysate, can be partially purified, or can be purified to homogeneity. It is preferred that the mutant acylase be immobilized. Typical immobilization supports for use herein include celite, dicalite, or UOP Beads.

The following examples are further illustrative of the present invention. These examples are not intended to limit the scope of the present invention, but provide further understanding of the invention.

In the following examples, some reagents, restriction enzymes, and other materials were obtained from commercial sources and used according to the indication by suppliers. Operations employed for the purification, characterization and the cloning of DNA are well known in the art and can be adapted from published literature.

EXAMPLE 1

Site-specific Mutagenesis

At selected positions, amino acid mutations were generated using the PCR site-directed method described above. The oligonucleotides used for introducing the desired mutations were obtained commercially. In particular the oligonucleotides have the following sequences:

(1) 5'CAGAGAAGCGGTTTGCCGCGGTGCCCCA-CAAATATC3' (SEQ.ID.NO.:15)—A:142 MET—ALA (2) 5'CGCTAGTGCTATCAGAGGCGCGGTTTGC-CATGGTGCC3' (SEQ.ID.NO.:16)—A:146 PHE—ALA (3) 5'AGCCAGGCCCATACCAGCCCTGCGGAC-CATTTACCATG3' (SEQ.ID.NO.:17)—B:24 PHE—ALA (4) 5'AGCCAGGCCCATACCAGCCCAACTGCG-GACCATTTACCATG3' (SEQ.ID.NO.:18)—B:24 PHE—VAL (5) 5'AGCCAGGCCCATACCAGCCGAACTGCG-GACCATTTACCATG3' (SEQ.ID.NO.:19)—B:24 PHE—LEU (6) 5'AGCCAGGCCCATACCAGCCCCACTGCG-GACCATTTACCATG3' (SEQ.ID.NO.:20)—B:24 PHE—GLY (7) 5'AGCCAGGCCCATACCAGCCATCCTGCG-GACCATTTACCATG3' (SEQ.ID.NO.:21)—B:24 PHE—MET (8) 5'AGCCAGGCCCATACCAGCCACACTGCG-GACCATTTACCATG3' (SEQ.ID.NO.:22)—B:24 PHE—CYS (9) 5'AGCCAGGCCCATACCAGCCAGACTGCG-GACCATTTACCATG3' (SEQ.ID.NO.:23)—B:24 PHE—SER

(10) 5'AGCCAGGCCCATACCAGCCGGTCTGCG-GACCATTTACCATG3' (SEQ.ID.NO.:24)—B:24 PHE—PRO

(11) 5'AGCCAGGCCCATACCAGCCCTGCTGCG-GACCATTTACCATG3' (SEQ.ID.NO.:25)—B:24 PHE—ASP

(12) 5'AGCCAGGCCCATACCAGCCGTGCTGCG-GACCATTTACCATG3' (SEQ.ID.NO.:26)—B:24 PHE—HIST

(13) 5'AGCCAGGCCCATACCAGCCATACTGCG-GACCATTTACCATG3' (SEQ.ID.NO.:27)—B:24 PHE—TYR

(14) 5'AGCCAGGCCCATACCAGCCTTTCTGCG-GACCATTTACCATG3' (SEQ.ID.NO.:28)—B:24 PHE—LYS

(15) 5'AGCCAGGCCCATACCAGCCCCTCTGCG-GACCATTTACCATG3' (SEQ.ID.NO.:29)—B:24 PHE—ARG

(16) 5'CACACCATTATGACCAAAAGACAGC-CAGGATAGGCAAAT3' (SEQ.ID.NO.:30)—B: 56 VAL—SER

(17) 5'CACACCATTATGACCAAAAGTCAGC-CAGGATAGGCAAAT3' (SEQ.ID.NO.:31)—B: 56 VAL—THRE

(18) 5'GCGAAACAAGCACTGGACCTTCAAACTG-GTACTATGCTG3' (SEQ.ID.NO.:32)—B: 177ILE—PHE

(19) 5'AGCCAGGCCCATACCAGCCAATCTGCG-GACCATTTACCATG3' (SEQ. ID NO.:33)—B: 24 PHE—ILE

(20) 5'AGCCAGGCCCATACCAGCCAGTCTGCG-GACCATTTACCATG3' (SEQ. ID. NO.:34)—B: 24 PHE—THR

(21) 5'AGCCAGGCCCATACCAGCCTTGCTGCG-GACCATTTACCATG3' (SEQ. ID. NO.:35)—B: 24 PHE—GLN

(22) 5'AGCCAGGCCCATACCAGCCATTCTGCG-GACCATTTACCATG3' (SEQ. ID. NO.:36)—B: 24 PHE—ASN

(23) 5'AGCCAGGCCCATACCAGCCTTCCTGCG-GACCATTTACCATG3' (SEQ. ID. NO.:37)—B 24 PHE—GLU

(24) 5'AGCCAGGCCCATACCAGCCCCACTGCG-GACCATTTACCATG3' (SEQ. ID. NO.:38)—B 24 PHE—TRP (1) The gene for penicillin G acylase is inserted into the PBM plasmid (FIG. 3) which is used as a template for the synthesis of the mutated gene.

(2) An oligonucleotide is designed which is complementary to the sequence to be mutagenized except for an internal portion which determines the mutation.

(3) Using standard PCR techniques, the synthetic oligonucleotide is annealed to the template and the template is amplified. The megaprimer product is purified to be used for a second round of PCR to generate the double-stranded mutant. The mutant DNA is then purified from a preparative agarose gel.

EXAMPLE 2

Cloning and Expression of Mutant Penicillin G Acylases

The mutated penicillin G acylase gene is cloned into plasmid PBM which contains the tac promoter and is induced by lactose or IPTG. The recombinant plasmids can be introduced into a host organism selected from the *E. coli* group. These microorganisms are then cultivated under appropriate conditions and colonies selected.

(1) Both the PBM plasmid and the DNA sequence encoding the mutagenized enzyme are digested with the restriction enzymes HindIII and BamHI. The products are gel purified.

(2) The digested DNA sequences are ligated and an aliquot of the ligation reaction is used to transform competent *E. coli* cells. The transformants were subsequently selected on LB plates containing kanamycin and lactose.

(3) To assay, individual colonies were chosen and grown overnight at 28° C. in LB media containing lactose and kanamycin.

(4) To verify the mutations, a kit from Ambion Inc. was utilized. This method is based on the fact that certein RNases can selectively cleave double stranded RNA at a position with a single mismatched base pair, indicating mutation has occured.

EXAMPLE 3

Culture of Microorganism

Transformed *E. coli* colonies are used to inoculate seed cultures into 500 ml Erlenmeyer flasks containing 100 ml of Luria Bertuni medium broth supplemented with 30 µg/ml of kanamycin. Seed flasks are cultured for 5 hours at 28° C. 50 ml of culture is used to inoculate 2 liter tanks. The base media is 0.3% $K_2HPO_4$, 0.2% $KH_2PO_4$, 0.2% $MgSO_4$, 0.05% $(NH_4)_2SO_4$, 0.003% $FeSO_4$, 0.001% $MnSO_4$, 0.3% yeast extract, and 30 µg/ml of kanamycin. The pH is 6.8–7.2. The tanks are run in a pH-regulated feeding profile. The tanks are supplemented with 20% NZ amine, 20% glucose, and kanamycin. The fermentor broth was cultured for 44 hours at 30° C. with high aeration.

EXAMPLE 4

Isolation and Immobilization of Penicillin G acylase from *E coli*

The whole broth was microfluidized to break open cells. 10% Celite was added and 0.2–0.25% of PEI was added to clarify the broth. The mixture was stirred for one hour, filtered, and washed with an equal volume of water to give a clarified broth. The clarified broth was ultrafiltered through a 30,000 MWCO membrane to 5% of its original volume.

(1) Immobilization to UOP-aluminum beads

Shake the ultrafiltered broth with UOP beads overnight at 10° C. Wash beads with water and store at 4° C.

(2) Immobilization to Diacalite

4% Triton X-100, 5% Biocryl and isopropanol to 30% were added to the ultrafiltered broth and the mixture stirred for 1 hour and filtered. To the filtrate 1% Speedplus was added and 50% PEG was added to a final concentration of 15%, the mixture was stirred for 15 minutes and 50% glutaraldehyde was added to a final concentration of 0.4%. The immobilization was allowed to proceed for 15 minutes at room temperature. The enzyme was filtered and washed with water until the wash was colorless. The pH was maintained between 7.2 nd 7.6 throughout the procedure.

EXAMPLE 5

Assay of Hydrolytic Activity of Penicillin G acylases (1) Assay with the commercial substrate, 6-nitro-3-(phenyl-acetamido) benzoic acid.

20 µl samples of cell culture are added to wells of a 96-well microtiterplate which contains 0.1% of the substrate in 0.2M potassium phosphate buffer, pH 7.4. The reaction is followed spectrophotometrically at 405 nm.

2. Assay with p-Dimethyl-Aminobenzaldehyde (p-DAB):

Sonicate 1 ml cell/ culture sample and add 1 ml 4.5% K penicillin G in 200 mM potassium phosphate buffer (pH 7.5). Incubate 15 minutes at 37° C. with shaking. Add 1 ml 99.0% acetonitrile and 1.0% acetic acid. Mix and centrifuge. To 1 ml of supernatant add 3 ml p-DAB reagent. (To prepare p-DAB Reagent; combine 1 part 10 mg/ml p-DAB and 6 parts sodium acetate buffer). Incubate 4 minutes and read at 415 nm. Calculate IU/ml using a standard factor of 100 µg/ml of 6APA.

EXAMPLE 6

Assay of Synthetic Activity of Penicillin G acylases (1) Cefadroxil:

Dissolve 10.5 g hydroxyethyl ester hydrochlorides salt of p-hydroxyphenylglycine in 37.5 ml water. Adjust pH to 8.0 with ammonium hydroxide. Add 4.8 g 7-ADCA and dissolve (pH 7.5). Adjust pH to 7.0 with 6N HCl. Bring volume to 60 ml. Divide reaction mix into 12 equal parts of 5 ml each. Add immobilized penicillin G acylase to a final concentration of 40 IU/ml. Remove aliquots at designated times for HPLC assay.

(2) cefprozil Synthesis

Add 4.5 g ester salt to 60 ml of water, pH to 8.26. Add 3.6 g 7-PACA. Add 1.72 ml ammonium hydroxide to pH 8.26. Add 4.5 g ester, salt pH to 7.56. Divide reaction mix into 12 equal parts. Add immobilized Penicillin G acylase to a final concentrations of 40 IU/ml. Remove aliquots at designated times for HPLC assay (3) Amoxicillin Assay Add 3.5g of ester salt to 12.5 ml of water. pH to 8.0 with ammonium hydroxide. Add 1.6 g 6-APA, dissolve and pH to 7.0. Bring volume to 20 ml. Divide reaction mix into 4 equal parts of 5 ml. Add immobilized penicillin G acylase to a final concentration of 40 IU/ml. Remove aliquots at designated times for HPLC assay.

(4) HPLC assays

Samples are manipulated as follows: To 200 μl of sample, add 1 ml of 20 mM KP buffer, pH 7.4, spin & remove 200 μl of supernatant to HPLC vials. Add 800 μl of buffer and inject 10 μl for assay. The HPLC assays for each reaction are illustrated in Table 1.

TABLE 1

HPLC procedures for analysis of composition of enzyme reaction mixtures for synthesis of β-lactam antibiotics

| ANTIBIOTIC | COLUMN | SOLVENT |
|---|---|---|
| Cefprozil and Amoxicillin | Micro-Bondapak C-18, 30 cm × 0.25 inch, Waters Associates | 0.1 N potassium hydroxide 0.00693 M tetrabutylammonium hydroxide 10% methanol, pH 7.0 |
| Cefprozil | Phenomenex Phenosphere ODS % micron, 4.6 mm × 5.0 cm | 24% acetonitrile, 0.16% KH$_2$PO$_4$, 0.2% NaSDS pH 2.6 |

The mutant of penicillin G acylase with an alanine substituted for phenylalanine 24 on the beta subunit was found to demonstrate superior synthesis for β-lactam antibiotics although it exhibited 25% of the hydrolytic activity. This mutant penicillin G acylase will be designated as F1. These results are demonstrated in Tables 2–12.

TABLE 2

Synthesis vs Hydrolysis activity of wild-type and mutant Penicillin G acylases

| MUTANT | HYDROLYSIS | SYNTHESIS |
|---|---|---|
| Wild-type | 100% | 100% |
| Met 142-Ala | 10% | 0% |
| Val 56-Thr | 4% | 127% |
| Phe146-Ala | 5% | 0% |
| Phe24-Ala | 25% | 330% |
| Phe24-Val | 36% | 3% |
| Phe24-Leu | 80% | 229% |

25 ml cultures were inoculated into Luria-Bertaini broth containing 30 μg/ml kanamycin and shaken overnight at 28° C. Cultures were induced with 800 μm IPTG for 4 hours. Cells were concentrated 10 fold and sonicated.

Hydrolysis was determined by microtitre plate assay. The substrate was 0.1% nitro-(phenyl-acetamido) benzoic acid in 0–0.2 M potassium phosphate buffer. The data is expressed as % of wild-type.

Synthesis was determined by formation of cefadroxil after 4 hours of incubation with hydroxy ethyl ester and 7 ADCA. The assay was performed by HPLC. The activity is expressed as % of wild-type.

TABLE 3

The beta 24 postition (phenylalanine) on Penicillin G acylase has been substituted with each possible amino acid. The synthetic and hydrolytic activity for each construct has been analyzed in three separate experiments. The averaged data is listed below:

| Amino Acid Change | Hydrolysis | Synthesis |
|---|---|---|
| Alanine | 22% | 330% |
| Valine | 36% | 3% |
| Leucine | 80% | 227% |
| Aspartic acid | 10% | 4% |

TABLE 3-continued

The beta 24 postition (phenylalanine) on Penicillin G acylase has been substituted with each possible amino acid. The synthetic and hydrolytic activity for each construct has been analyzed in three separate experiments. The averaged data is listed below:

| Amino Acid Change | Hydrolysis | Synthesis |
|---|---|---|
| Histidine | 7% | 6% |
| Lysine | 5% | 0 |
| Methionine | 7% | 0 |
| Proline | 8% | 31% |
| Serine | 39% | 23% |
| Tyrosine | 2% | 0 |
| Arginine | 7% | 4% |
| Asparagine | 8% | 6% |
| Glutamic acid | 7% | 0 |
| Glutamine | 3% | 28% |
| Isoleucine | 8% | 4% |
| Threonine | 20% | 6% |
| Tyrptophan | 9% | 9% |
| Glycine | 27% | 19% |
| Cysteine | 26% | 0% |
| Alanine + Val(B)56-Thr | 0% | 0% |
| Leucine + Val(B)56-Thr | 6% | 0% |

TABLE 4

Effects of Temperature on the Synthetic Yield of Cefprozil
The reaction is run at pH 7.5 with 2.3 molar equivalents of ester to 7-PACA
The percent conversion of 7PACA to cefprozil in 120 minutes is reported.

| Temperature | Wild-Type PGA | F1 Mutant PGA |
|---|---|---|
| 37° C. | 80% | 99% |
| Room Temperature | 85% | 98% |
| 10° C. | 90% | 100% |

TABLE 5

Effects of Temperature on the Synthetic Yield of Cefadroxil
The reaction is run at pH 7.0 with 1.9 molar equivalents of ester to 7-ADCA
The percent conversion of 7-ADCA to cefadroxil in 120 minutes is reported.

| Temperature | Wild-Type PGA | F1 Mutant PGA |
|---|---|---|
| 37° C. | 79% | 95% |
| Room Temperature | 86% | 91% |
| 10° C. | 83% | 95% |

TABLE 6

Effects of Enzyme Concentration on the Synthetic Yield of Cefprozil
The reaction is run at pH 7.5, room temperature, with 2.3 molar equivalents of ester to 7-PACA.
The percent conversion of 7-PACA to cefprozil in 120 minutes is reported.

| Gram of immobilized enzyme | Wild-Type PGA | F1 Mutant PGA |
|---|---|---|
| 0.4 g | 88% | 100% |
| 0.2 g | 90% | 100% |
| 0.1 g | 90% | 98% |

TABLE 7

Effects of Enzyme Concentrations on the Synthetic Yield of Cefadroxil
The reaction is run at pH 7.0, room temperature, with 1.9 molar equivalents of ester to 7-ADCA.
The percent conversion of 7-PACA to cefprozil in 120 minutes is reported.

| Gram of immobilized enzyme | Wild-Type PGA | F1 Mutant PGA |
| --- | --- | --- |
| 0.7 g | 89% | 95% |
| 0.35 g | 81% | 97% |
| 0.175 g | 79% | 97% |

TABLE 8

Effects of Acyl Donor Concentration on the Synthetic Yield of Cefprozil
The reaction is run at pH 6.5 and at room temperature.
0.2 g of immobilized enzyme is added to reactions.
The percent conversion of 7-PACA to cefprozil in 120 minutes is reported.

| Molar eqnivalent of ester to 7-PACA | Wild-Type PGA | F1 Mutant PGA |
| --- | --- | --- |
| 2.3 | 91% | 100% |
| 1.5 | 86% | 99% |
| 1.45 | 83% | 99% |
| 1.38 | 83% | 99% |
| 1.3 | 85% | 99% |
| 1.2 | 80% | 96% |

TABLE 9

Effects of Acyl Donor Concentration on the
Synthetic Yield of Cefadroxil
The reaction is run at pH 7.0 and at room temperature.
0.2 g of immobilized enzyme is added to reactions.
The percent conversion of 7-ADCA to cefadroxil
in 120 minute is reported.

| Molar eqnivalent of ester to 7-PACA | Wild-Type PGA | F1 Mutant PGA |
| --- | --- | --- |
| 1.89 | 81% | 96% |
| 1.63 | 73% | 90% |

TABLE 10

Wild-type vs Mutant Penicillin G acylase semisyntbesis of Amoxicllin

| WT PGA | | F1 PGA | |
| --- | --- | --- | --- |
| % 6APA Remaining | % Ester Remaining | % 6APA Remaining | % Ester Remaining |
| 58 | 62 | 52 | 58 |
| 30 | 27 | 12 | 4 |
| 20 | 17 | 9 | 1 |

TABLE 11

Optimized Conditions for the Semisynthesis of Cefprozil

| Temperature | Room temperature |
| --- | --- |
| pH | 6.5 |
| Ester Concentration | 1.2–1.3 molar equivalents |
| Enzyme Concentration | 0.2 g in a 5 ml volume |

TABLE 12

Optimized Condition for the Semisynthesis of Cefadroxil

| Temperature | Room temperature |
| --- | --- |
| pH | 7.0 |
| Ester Concentration | 1.8 molar equivalents |
| Enyme Concentration | 0.2 g in a 5 ml volume |

What is claimed is:

1. A mutant type II *E. coli* penicillin G acylase comprising an amino acid substitution of PheB24-Ala, wherein said position B24 corresponds to the amino acid position 24 of SEQ ID No:4.

2. A mutant *E. coli* penicillin G acylase comprising an amino acid substitution at one or more of the following:

Met at A142 to Ala;
Phe at A146 to Ala;
Phe at B24 to Ala, Leu, Val, Pro, Tyr, Met, Ser, Cys, Gly, Asp,
Lys, Arg, Thr, Trp, Ile, Glu, Gln, Asn, or His;
Val at B5 to Ser or Thr;
Ile at B177 to Phe;
wherein said positions A142 and A146 correspond to the amino acid positions 142 and 146 of SEQ ID NO:2 and wherein said positions B24, B56 and B177 correspond to the amino acid positions 24, 56 and 177 of SEQ ID NO:4;
said mutant acylase further comprising a truncation of the N-terminus of the alpha subunit by 1 or 2 amino acids, or a truncation of the C-terminus of the alpha subunit by 10 to 15 amino acids, or a truncation of both the N-terminus of the alpha subunit by 1 or 2 amino acids and a truncation of the C-terminus of the alpha subunit by 10 to 15 amino acids, wherein said alpha subunit has an amino acid sequence corresponding to the amino acid sequence set forth in SEQ ID NO:2.

3. The mutant acylase of claim 2 comprising an amino acid substitution of PheB24-Ala.

4. The mutant acylase of claim 2 comprising an amino acid substitution of PheB24-Leu.

5. The mutant acylase of claim 2 wherein the C-terminus of the alpha subunit is truncated by 12 or 13 amino acids.

6. A mutant type II *E. coli* penicillin G acylase comprising an amino acid substitution of PheB24-Leu, wherein said position B24 corresponds to the amino acid position 24 of SEQ ID No:4.

7. A nucleic acid sequence encoding the mutant acylase of claim 1, claim 2, claim 5, claim 3, claim 4, or claim 6.

8. An expression vector comprising a nucleic acid sequence as defined in claim 7 operably linked to a promoter sequence capable of directing its expression in host cell.

9. A host cell comprising the expression vector of claim 8.

10. A process for producing a mutant penicillin G acylase comprising culturing the host cell of claim 9 under conditions suitable for production of the mutant acylase.

11. A process for producing a semi-synthetic 6-acylated penicillanic acid, a 7-acylated cephalosporanic acid or a salt or ester thereof which comprises contacting a corresponding 6-amino β-lactam or 7-ACA or salt or ester thereof, respectively, and an acylating agent with a mutant acylase as defined in claim 1, claim 2, claim 5, claim 3, claim 4, or claim 6 under conditions suitable for acylation to occur.

12. The process of claim 11 wherein said mutant acylase is immobilized.

13. A process for producing a semi-synthetic 6-acylated penicillanic acid, a 7-acylated cephalosporanic acid, a 7-acylated desacetoxycephalosporanic acid, or a salt or ester thereof which comprises contacting a corresponding 6-amino penicillanic acid, 7-amino cephalosporanic acid, 7-amino desacetoxycephalosporanic acid, or a salt or ester thereof, respectively, and an acylating agent with a mutant acylase as defined in claim 1, claim 2, claim 5, claim 3, claim 4, or claim 6 under conditions suitable for acylation to occur.

14. The process of claim 13 wherein said acylating agent is hydroxyethyl ester p-hydroxyphenylglycine or a salt thereof.

15. A process for producing a semi-synthetic 7-acylated cephalosporanic acid or a salt or ester thereof which comprises contacting 7-ACA or a salt or ester thereof and an acylating agent with a mutant acylase as defined in claim 1, claim 2, claim 5, claim 3, claim 4, or claim 6 under conditions suitable for acylation to occur.

16. A process for producing a semi-synthetic 7-acylated desacetoxycephalosporanic acid or a salt or ester thereof which comprises contacting 7-ADCA or a salt or ester thereof and an acylating agent with a mutant acylase as defined in claim 1, claim 2, claim 5, claim 3, claim 4 or claim 6 under conditions suitable for acylation to occur.

17. The process of claim 16 wherein said semi-synthetic 7-acylated desacetoxycephalosporanic acid is cefadroxil.

18. A process for producing a semi-synthetic 7-acylated propenylcephalosporanic acid or a salt or ester thereof which comprises contacting 7-PACA or a salt or ester thereof and an acylating agent with a mutant acylase as defined in claim 1, claim 2, claim 5, claim 3, claim 4, or claim 6 under conditions suitable for acylation to occur.

19. The process of claim 18 wherein said semi-synthetic 7-acylated propenylcephalosporanic is cefprozil.

20. A process for producing a semi-synthetic 6-acylated penicillanic acid or a salt or ester thereof which comprises contacting 6-APA or a salt or ester thereof and an acylating agent with a mutant acylase as defined in claim 1, claim 2, claim 5, claim 3, claim 4 or claim 6 under conditions suitable for acylation to occur.

21. The process of claim 20 wherein said semi-synthetic 6-acylated penicillanic acid is amoxicillin.

22. A process for deacylating a 6-acylated penicillanic acid, a 7-acylated cephalosporanic acid, or a 7-acylated desacetoxycephalosporanic acid, or a salt or ester thereof, to form the corresponding 6-amino penicillanic acid, 7-amino cephalosporanic acid, or 7-amino desacetoxycephalosporanic acid, or a salt or ester thereof, respectively, which comprises contacting said 6-acylated, 7-acylated, or 7-acylated desacetoxy compound with a mutant acylase as defined in claim 1, claim 2, claim 5, claim 3, claim 4, or claim 6 under conditions suitable for deacylation to occur.

23. A process for deacylating a phenylacetyl derivative or a salt or ester thereof comprising contacting said phenylacetyl derivative or salt or ester thereof with a mutant acylase as defined in claim 1, claim 2, claim 5, claim 3, claim 4, or claim 6 under conditions suitable for deacylation to occur.

24. The process of claim 23 where said phenylacetyl derivative is penicillin G.

* * * * *

SEQUENCE LISTING

<160> NUMBER OF SEQ ID NOS: 38

<210> SEQ ID NO 1
<211> LENGTH: 627
<212> TYPE: DNA
<213> ORGANISM: Escherichia coli
<220> FEATURE:
<221> NAME/KEY: CDS
<222> LOCATION: (1)..(627)

<400> SEQUENCE: 1

```
gag cag tcg tca agt gag ata aag att gtt cgc gat gaa tac ggc atg      48
Glu Gln Ser Ser Ser Glu Ile Lys Ile Val Arg Asp Glu Tyr Gly Met
  1               5                  10                  15 ccg cat att tat gcc aat gat aca tgg cac cta ttt tat ggc tat ggc      96
Pro His Ile Tyr Ala Asn Asp Thr Trp His Leu Phe Tyr Gly Tyr Gly
             20                  25                  30
```

```
tat gta gta gca caa gat cgc ctt ttt cag atg gaa atg gca cgt cgc      144
Tyr Val Val Ala Gln Asp Arg Leu Phe Gln Met Glu Met Ala Arg Arg
            35                  40                  45 agt act caa ggg act gtc gcg gaa gtg ctt ggc aaa gat ttt gtg aaa      192
Ser Thr Gln Gly Thr Val Ala Glu Val Leu Gly Lys Asp Phe Val Lys
 50                  55                  60 ttt gat aaa gat atc cgt cgt aac tac tgg ccg gat gct atc cgg gcg      240
Phe Asp Lys Asp Ile Arg Arg Asn Tyr Trp Pro Asp Ala Ile Arg Ala
 65                  70                  75                  80 caa att gct gcc ctt tcc cca gag gat atg tcc att ctg caa ggc tac      288
Gln Ile Ala Ala Leu Ser Pro Glu Asp Met Ser Ile Leu Gln Gly Tyr
                 85                  90                  95 gct gat gga atg aat gcc tgg att gat aag gta aat acc aat cca gag      336
Ala Asp Gly Met Asn Ala Trp Ile Asp Lys Val Asn Thr Asn Pro Glu
            100                 105                 110 acg ctc tta cca aaa cag ttt aat aca ttt ggc ttt act cct aag cgc      384
Thr Leu Leu Pro Lys Gln Phe Asn Thr Phe Gly Phe Thr Pro Lys Arg
        115                 120                 125 tgg gaa ccg ttt gat gtc gcg atg ata ttt gtg ggc acc atg gca aac      432
Trp Glu Pro Phe Asp Val Ala Met Ile Phe Val Gly Thr Met Ala Asn
130                 135                 140 cgc ttc tct gat agc act agc gaa att gat aat ctg gca ctg cta acg      480
Arg Phe Ser Asp Ser Thr Ser Glu Ile Asp Asn Leu Ala Leu Leu Thr
145                 150                 155                 160 gct tta aaa gat aaa tat ggt gta tca caa ggc atg gcg gta ttt aat      528
Ala Leu Lys Asp Lys Tyr Gly Val Ser Gln Gly Met Ala Val Phe Asn
                165                 170                 175 cag ttg aaa tgg ctg gta aac cca tca gcg cca acc act att gcc gta      576
Gln Leu Lys Trp Leu Val Asn Pro Ser Ala Pro Thr Thr Ile Ala Val
            180                 185                 190 caa gag agt aac tac cca ctt aaa ttt aat cag caa aac tcg caa aca      624
Gln Glu Ser Asn Tyr Pro Leu Lys Phe Asn Gln Gln Asn Ser Gln Thr
        195                 200                 205 gca                                                                  627
Ala
```

<210> SEQ ID NO 2
<211> LENGTH: 209
<212> TYPE: PRT
<213> ORGANISM: Escherichia coli

<400> SEQUENCE: 2

```
Glu Gln Ser Ser Glu Ile Lys Ile Val Arg Asp Glu Tyr Gly Met
 1               5                  10                  15

Pro His Ile Tyr Ala Asn Asp Thr Trp His Leu Phe Tyr Gly Tyr Gly
            20                  25                  30

Tyr Val Val Ala Gln Asp Arg Leu Phe Gln Met Glu Met Ala Arg Arg
            35                  40                  45

Ser Thr Gln Gly Thr Val Ala Glu Val Leu Gly Lys Asp Phe Val Lys
 50                  55                  60

Phe Asp Lys Asp Ile Arg Arg Asn Tyr Trp Pro Asp Ala Ile Arg Ala
 65                  70                  75                  80

Gln Ile Ala Ala Leu Ser Pro Glu Asp Met Ser Ile Leu Gln Gly Tyr
                 85                  90                  95

Ala Asp Gly Met Asn Ala Trp Ile Asp Lys Val Asn Thr Asn Pro Glu
            100                 105                 110

Thr Leu Leu Pro Lys Gln Phe Asn Thr Phe Gly Phe Thr Pro Lys Arg
        115                 120                 125
```

-continued

```
Trp Glu Pro Phe Asp Val Ala Met Ile Phe Val Gly Thr Met Ala Asn
    130                 135                 140

Arg Phe Ser Asp Ser Thr Ser Glu Ile Asp Asn Leu Ala Leu Leu Thr
145                 150                 155                 160

Ala Leu Lys Asp Lys Tyr Gly Val Ser Gln Gly Met Ala Val Phe Asn
            165                 170                 175

Gln Leu Lys Trp Leu Val Asn Pro Ser Ala Pro Thr Thr Ile Ala Val
            180                 185                 190

Gln Glu Ser Asn Tyr Pro Leu Lys Phe Asn Gln Gln Asn Ser Gln Thr
        195                 200                 205

Ala

<210> SEQ ID NO 3
<211> LENGTH: 1674
<212> TYPE: DNA
<213> ORGANISM: Escherichia coli
<220> FEATURE:
<221> NAME/KEY: CDS
<222> LOCATION: (1)..(1674)

<400> SEQUENCE: 3 agc aat atg tgg gtg atc ggc aaa agc aaa gcc cag gat gcg aaa gca       48
Ser Asn Met Trp Val Ile Gly Lys Ser Lys Ala Gln Asp Ala Lys Ala
 1               5                  10                  15 atc atg gta aat ggt ccg cag gct ggc tgg tat gcg cct gcg tat act      96
Ile Met Val Asn Gly Pro Gln Ala Gly Trp Tyr Ala Pro Ala Tyr Thr
                 20                  25                  30 tat ggt att ggt ctg cac ggt gct ggt tat gat gtc act ggc aat aca     144
Tyr Gly Ile Gly Leu His Gly Ala Gly Tyr Asp Val Thr Gly Asn Thr
             35                  40                  45 cca ttt gcc tat cct ggg ctg gtt ttt ggt cat aat ggt gtg att tcc     192
Pro Phe Ala Tyr Pro Gly Leu Val Phe Gly His Asn Gly Val Ile Ser
         50                  55                  60 tgg gga tca acg gca ggt ttc ggc gat gat gtc gat att ttt gct gaa     240
Trp Gly Ser Thr Ala Gly Phe Gly Asp Asp Val Asp Ile Phe Ala Glu
 65                  70                  75                  80 cgg ctg tcg gca gag aaa cca ggc tac tac ttg cat aat ggt aag tgg     288
Arg Leu Ser Ala Glu Lys Pro Gly Tyr Tyr Leu His Asn Gly Lys Trp
                 85                  90                  95 gtg aaa atg tta agc cgt gag gaa acc att acg gtg aaa aat ggt cag     336
Val Lys Met Leu Ser Arg Glu Glu Thr Ile Thr Val Lys Asn Gly Gln
                100                 105                 110 gca gag acc ttt act gtc tgg cgt acg gtg cat ggc aac att ctc caa     384
Ala Glu Thr Phe Thr Val Trp Arg Thr Val His Gly Asn Ile Leu Gln
            115                 120                 125 act gac cag acg aca caa acg gct tac gct aaa tcc cgc gca tgg gat     432
Thr Asp Gln Thr Thr Gln Thr Ala Tyr Ala Lys Ser Arg Ala Trp Asp
        130                 135                 140 ggt aaa gag gtg gcg tct ttg ctg gcc tgg act cat cag atg aag gcc     480
Gly Lys Glu Val Ala Ser Leu Leu Ala Trp Thr His Gln Met Lys Ala
145                 150                 155                 160 aaa aat tgg cag gag tgg aca cag cag gcg aaa caa gca ctg acc         528
Lys Asn Trp Gln Glu Trp Thr Gln Gln Ala Lys Gln Ala Leu Thr
                165                 170                 175 atc aac tgg tac tat gct gat gta aac ggc aat att ggt tat gtt cat     576
Ile Asn Trp Tyr Tyr Ala Asp Val Asn Gly Asn Ile Gly Tyr Val His
            180                 185                 190 act ggt gct tat cca gat cgt caa tca ggc cat gat ccg cga tta ccc     624
Thr Gly Ala Tyr Pro Asp Arg Gln Ser Gly His Asp Pro Arg Leu Pro
```

-continued

```
            195                 200                 205
gtt cct ggt acg gga aaa tgg gac tgg aaa ggg cta ttg cct ttt gaa    672
Val Pro Gly Thr Gly Lys Trp Asp Trp Lys Gly Leu Leu Pro Phe Glu
210                 215                 220 atg aac cct aag gtg tat aac ccc cag tcg gga tat att gct aac tgg    720
Met Asn Pro Lys Val Tyr Asn Pro Gln Ser Gly Tyr Ile Ala Asn Trp
225                 230                 235                 240 aac aat tct ccc caa aaa gat tat ccc gct tca gat ctg ttt gcc ttt    768
Asn Asn Ser Pro Gln Lys Asp Tyr Pro Ala Ser Asp Leu Phe Ala Phe
                245                 250                 255 ttg tgg ggt ggt gca gat cgc gtt acg gag atc gac cga ctg ctt gag    816
Leu Trp Gly Gly Ala Asp Arg Val Thr Glu Ile Asp Arg Leu Leu Glu
            260                 265                 270 caa aag cca cgc tta act gct gat cag gca tgg gat gtt att cgc caa    864
Gln Lys Pro Arg Leu Thr Ala Asp Gln Ala Trp Asp Val Ile Arg Gln
        275                 280                 285 acc agt cgt cag gat ctt aac ctg agg ctt ttt tta cct act ctg caa    912
Thr Ser Arg Gln Asp Leu Asn Leu Arg Leu Phe Leu Pro Thr Leu Gln
    290                 295                 300 gca gcg aca tct ggt ttg aca cag agc gat ccg cgt cgt cag ttg gta    960
Ala Ala Thr Ser Gly Leu Thr Gln Ser Asp Pro Arg Arg Gln Leu Val
305                 310                 315                 320 gaa aca tta aca cgt tgg gat ggc atc aat ttg ctt aat gat gat ggt    1008
Glu Thr Leu Thr Arg Trp Asp Gly Ile Asn Leu Leu Asn Asp Asp Gly
                325                 330                 335 aaa acc tgg cag cag cca ggc tct gcc atc ctg aac gtt tgg ctg acc    1056
Lys Thr Trp Gln Gln Pro Gly Ser Ala Ile Leu Asn Val Trp Leu Thr
            340                 345                 350 agt atg ttg aag cgt acc gta gtg gct gcc gta cct atg cca ttt gat    1104
Ser Met Leu Lys Arg Thr Val Val Ala Ala Val Pro Met Pro Phe Asp
        355                 360                 365 aag tgg tac agc gcc agt ggc tac gaa aca acc cag gac ggc cca act    1152
Lys Trp Tyr Ser Ala Ser Gly Tyr Glu Thr Thr Gln Asp Gly Pro Thr
    370                 375                 380 ggt tcg ctg aat ata agt gtt gga gca aaa att ttg tat gag gcg gtg    1200
Gly Ser Leu Asn Ile Ser Val Gly Ala Lys Ile Leu Tyr Glu Ala Val
385                 390                 395                 400 cag gga gac aaa tca cca atc cca cag gcg gtt gat ctg ttt gct ggg    1248
Gln Gly Asp Lys Ser Pro Ile Pro Gln Ala Val Asp Leu Phe Ala Gly
                405                 410                 415 aaa cca cag cag gag gtt gtg ttg gct gcg ctg gaa gat acc tgg gag    1296
Lys Pro Gln Gln Glu Val Val Leu Ala Ala Leu Glu Asp Thr Trp Glu
            420                 425                 430 act ctt tcc aaa cgc tat ggc aat aat gtg agt aac tgg aaa aca cct    1344
Thr Leu Ser Lys Arg Tyr Gly Asn Asn Val Ser Asn Trp Lys Thr Pro
        435                 440                 445 gca atg gcc tta acg ttc cgg gca aat aat ttc ttt ggt gta ccg cag    1392
Ala Met Ala Leu Thr Phe Arg Ala Asn Asn Phe Phe Gly Val Pro Gln
    450                 455                 460 gcc gca gcg gaa gaa acg cgt cat cag gcg gag tat caa aac cgt gga    1440
Ala Ala Ala Glu Glu Thr Arg His Gln Ala Glu Tyr Gln Asn Arg Gly
465                 470                 475                 480 aca gaa aac gat atg att gtt ttc tca cca acg aca agc gat cgt cct    1488
Thr Glu Asn Asp Met Ile Val Phe Ser Pro Thr Thr Ser Asp Arg Pro
                485                 490                 495 gtg ctt gcc tgg gat gtg gtc gca ccc ggt cag agt ggg ttt att gct    1536
Val Leu Ala Trp Asp Val Val Ala Pro Gly Gln Ser Gly Phe Ile Ala
            500                 505                 510 ccc gat gga aca gtt gat aag cac tat gaa gat cag ctg aaa atg tac    1584
```

```
Pro Asp Gly Thr Val Asp Lys His Tyr Glu Asp Gln Leu Lys Met Tyr
        515                 520                 525 gaa aat ttt ggc cgt aag tcg ctc tgg tta acg aag cag gat gtg gag    1632
Glu Asn Phe Gly Arg Lys Ser Leu Trp Leu Thr Lys Gln Asp Val Glu
530                 535                 540 gcg cat aag gag tcg cag gaa gtg ttg cac gtt cag aga taa             1674
Ala His Lys Glu Ser Gln Glu Val Leu His Val Gln Arg
545                 550                 555
```

<210> SEQ ID NO 4
<211> LENGTH: 557
<212> TYPE: PRT
<213> ORGANISM: Escherichia coli

<400> SEQUENCE: 4

```
Ser Asn Met Trp Val Ile Gly Lys Ser Lys Ala Gln Asp Ala Lys Ala
1               5                   10                  15

Ile Met Val Asn Gly Pro Gln Ala Gly Trp Tyr Ala Pro Ala Tyr Thr
                20                  25                  30

Tyr Gly Ile Gly Leu His Gly Ala Gly Tyr Asp Val Thr Gly Asn Thr
            35                  40                  45

Pro Phe Ala Tyr Pro Gly Leu Val Phe Gly His Asn Gly Val Ile Ser
        50                  55                  60

Trp Gly Ser Thr Ala Gly Phe Gly Asp Asp Val Asp Ile Phe Ala Glu
65                  70                  75                  80

Arg Leu Ser Ala Glu Lys Pro Gly Tyr Tyr Leu His Asn Gly Lys Trp
                85                  90                  95

Val Lys Met Leu Ser Arg Glu Glu Thr Ile Thr Val Lys Asn Gly Gln
                100                 105                 110

Ala Glu Thr Phe Thr Val Trp Arg Thr Val His Gly Asn Ile Leu Gln
            115                 120                 125

Thr Asp Gln Thr Thr Gln Thr Ala Tyr Ala Lys Ser Arg Ala Trp Asp
        130                 135                 140

Gly Lys Glu Val Ala Ser Leu Leu Ala Trp Thr His Gln Met Lys Ala
145                 150                 155                 160

Lys Asn Trp Gln Glu Trp Thr Gln Gln Ala Lys Gln Ala Leu Thr
                165                 170                 175

Ile Asn Trp Tyr Tyr Ala Asp Val Asn Gly Asn Ile Gly Tyr Val His
                180                 185                 190

Thr Gly Ala Tyr Pro Asp Arg Gln Ser Gly His Asp Pro Arg Leu Pro
            195                 200                 205

Val Pro Gly Thr Gly Lys Trp Asp Trp Lys Gly Leu Leu Pro Phe Glu
        210                 215                 220

Met Asn Pro Lys Val Tyr Asn Pro Gln Ser Gly Tyr Ile Ala Asn Trp
225                 230                 235                 240

Asn Asn Ser Pro Gln Lys Asp Tyr Pro Ala Ser Asp Leu Phe Ala Phe
                245                 250                 255

Leu Trp Gly Gly Ala Asp Arg Val Thr Glu Ile Asp Arg Leu Leu Glu
                260                 265                 270

Gln Lys Pro Arg Leu Thr Ala Asp Gln Ala Trp Asp Val Ile Arg Gln
            275                 280                 285

Thr Ser Arg Gln Asp Leu Asn Leu Arg Leu Phe Leu Pro Thr Leu Gln
        290                 295                 300

Ala Ala Thr Ser Gly Leu Thr Gln Ser Asp Pro Arg Arg Gln Leu Val
305                 310                 315                 320
```

```
Glu Thr Leu Thr Arg Trp Asp Gly Ile Asn Leu Leu Asn Asp Asp Gly
                325                 330                 335
Lys Thr Trp Gln Gln Pro Gly Ser Ala Ile Leu Asn Val Trp Leu Thr
            340                 345                 350
Ser Met Leu Lys Arg Thr Val Ala Ala Val Pro Met Pro Phe Asp
        355                 360                 365
Lys Trp Tyr Ser Ala Ser Gly Tyr Glu Thr Thr Gln Asp Gly Pro Thr
    370                 375                 380
Gly Ser Leu Asn Ile Ser Val Gly Ala Lys Ile Leu Tyr Glu Ala Val
385                 390                 395                 400
Gln Gly Asp Lys Ser Pro Ile Pro Gln Ala Val Asp Leu Phe Ala Gly
            405                 410                 415
Lys Pro Gln Gln Glu Val Val Leu Ala Ala Leu Glu Asp Thr Trp Glu
        420                 425                 430
Thr Leu Ser Lys Arg Tyr Gly Asn Asn Val Ser Asn Trp Lys Thr Pro
    435                 440                 445
Ala Met Ala Leu Thr Phe Arg Ala Asn Phe Phe Gly Val Pro Gln
450                 455                 460
Ala Ala Ala Glu Glu Thr Arg His Gln Ala Glu Tyr Gln Asn Arg Gly
465                 470                 475                 480
Thr Glu Asn Asp Met Ile Val Phe Ser Pro Thr Thr Ser Asp Arg Pro
                485                 490                 495
Val Leu Ala Trp Asp Val Val Ala Pro Gly Gln Ser Gly Phe Ile Ala
            500                 505                 510
Pro Asp Gly Thr Val Asp Lys His Tyr Glu Asp Gln Leu Lys Met Tyr
        515                 520                 525
Glu Asn Phe Gly Arg Lys Ser Leu Trp Leu Thr Lys Gln Asp Val Glu
    530                 535                 540
Ala His Lys Glu Ser Gln Glu Val Leu His Val Gln Arg
545                 550                 555

<210> SEQ ID NO 5
<211> LENGTH: 27
<212> TYPE: DNA
<213> ORGANISM: Escherichia coli
<220> FEATURE:
<221> NAME/KEY: CDS
<222> LOCATION: (1)..(27)

<400> SEQUENCE: 5 ttt gtg ggc acc gcg gca aac cgc ttc                              27
Phe Val Gly Thr Ala Ala Asn Arg Phe
 1               5

<210> SEQ ID NO 6
<211> LENGTH: 9
<212> TYPE: PRT
<213> ORGANISM: Escherichia coli

<400> SEQUENCE: 6

Phe Val Gly Thr Ala Ala Asn Arg Phe
 1               5

<210> SEQ ID NO 7
<211> LENGTH: 27
<212> TYPE: DNA
<213> ORGANISM: Escherichia coli
<220> FEATURE:
<221> NAME/KEY: CDS
<222> LOCATION: (1)..(27)
```

-continued

<400> SEQUENCE: 7 atg gca aac cgc ttc tct gat agc act                                27
Met Ala Asn Arg Phe Ser Asp Ser Thr
 1               5

<210> SEQ ID NO 8
<211> LENGTH: 9
<212> TYPE: PRT
<213> ORGANISM: Escherichia coli

<400> SEQUENCE: 8

Met Ala Asn Arg Phe Ser Asp Ser Thr
 1               5

<210> SEQ ID NO 9
<211> LENGTH: 27
<212> TYPE: DNA
<213> ORGANISM: Escherichia coli
<220> FEATURE:
<221> NAME/KEY: CDS
<222> LOCATION: (1)..(27)

<400> SEQUENCE: 9 aat ggt ccg cag nnn ggc tgg tat gcg                                27
Asn Gly Pro Gln Xaa Gly Trp Tyr Ala
 1               5

<210> SEQ ID NO 10
<211> LENGTH: 9
<212> TYPE: PRT
<213> ORGANISM: Escherichia coli

<400> SEQUENCE: 10

Asn Gly Pro Gln Xaa Gly Trp Tyr Ala
 1               5

<210> SEQ ID NO 11
<211> LENGTH: 27
<212> TYPE: DNA
<213> ORGANISM: Escherichia coli
<220> FEATURE:
<221> NAME/KEY: CDS
<222> LOCATION: (1)..(27)

<400> SEQUENCE: 11 tat cct ggg ctg ast ttt ggt cat aat                                27
Tyr Pro Gly Leu Xaa Phe Gly His Asn
 1               5

<210> SEQ ID NO 12
<211> LENGTH: 9
<212> TYPE: PRT
<213> ORGANISM: Escherichia coli

<400> SEQUENCE: 12

Tyr Pro Gly Leu Xaa Phe Gly His Asn
 1               5

<210> SEQ ID NO 13
<211> LENGTH: 27
<212> TYPE: DNA
<213> ORGANISM: Escherichia coli
<220> FEATURE:
<221> NAME/KEY: CDS
<222> LOCATION: (1)..(27)

```
<400> SEQUENCE: 13 tat cct ggg ctg tct ttt ggt cat aat                              27
Tyr Pro Gly Leu Ser Phe Gly His Asn
  1               5

<210> SEQ ID NO 14
<211> LENGTH: 9
<212> TYPE: PRT
<213> ORGANISM: Escherichia coli

<400> SEQUENCE: 14

Tyr Pro Gly Leu Ser Phe Gly His Asn
  1               5

<210> SEQ ID NO 15
<211> LENGTH: 36
<212> TYPE: DNA
<213> ORGANISM: Escherichia coli

<400> SEQUENCE: 15
cagagaagcg gtttgccgcg gtgcccaca aatatc                           36

<210> SEQ ID NO 16
<211> LENGTH: 37
<212> TYPE: DNA
<213> ORGANISM: Escherichia coli

<400> SEQUENCE: 16
cgctagtgct atcagaggcg cggtttgcca tggtgcc                         37

<210> SEQ ID NO 17
<211> LENGTH: 38
<212> TYPE: DNA
<213> ORGANISM: Escherichia coli

<400> SEQUENCE: 17
agccaggccc ataccagccc tgcggaccat ttaccatg                        38

<210> SEQ ID NO 18
<211> LENGTH: 41
<212> TYPE: DNA
<213> ORGANISM: Escherichia coli

<400> SEQUENCE: 18
agccaggccc ataccagccc aactgcggac catttaccat g                    41

<210> SEQ ID NO 19
<211> LENGTH: 41
<212> TYPE: DNA
<213> ORGANISM: Escherichia coli

<400> SEQUENCE: 19
agccaggccc ataccagccg aactgcggac catttaccat g                    41

<210> SEQ ID NO 20
<211> LENGTH: 41
<212> TYPE: DNA
<213> ORGANISM: Escherichia coli

<400> SEQUENCE: 20
agccaggccc ataccagccc cactgcggac catttaccat g                    41

<210> SEQ ID NO 21
```

-continued

<210> SEQ ID NO 21
<211> LENGTH: 41
<212> TYPE: DNA
<213> ORGANISM: Escherichia coli

<400> SEQUENCE: 21
agccaggccc ataccagcca tcctgcggac catttaccat g                41

<210> SEQ ID NO 22
<211> LENGTH: 41
<212> TYPE: DNA
<213> ORGANISM: Escherichia coli

<400> SEQUENCE: 22
agccaggccc ataccagcca cactgcggac catttaccat g                41

<210> SEQ ID NO 23
<211> LENGTH: 41
<212> TYPE: DNA
<213> ORGANISM: Escherichia coli

<400> SEQUENCE: 23
agccaggccc ataccagcca gactgcggac catttaccat g                41

<210> SEQ ID NO 24
<211> LENGTH: 41
<212> TYPE: DNA
<213> ORGANISM: Escherichia coli

<400> SEQUENCE: 24
agccaggccc ataccagccg gtctgcggac catttaccat g                41

<210> SEQ ID NO 25
<211> LENGTH: 41
<212> TYPE: DNA
<213> ORGANISM: Escherichia coli

<400> SEQUENCE: 25
agccaggccc ataccagccc tgctgcggac catttaccat g                41

<210> SEQ ID NO 26
<211> LENGTH: 41
<212> TYPE: DNA
<213> ORGANISM: Escherichia coli

<400> SEQUENCE: 26
agccaggccc ataccagccg tgctgcggac catttaccat g                41

<210> SEQ ID NO 27
<211> LENGTH: 41
<212> TYPE: DNA
<213> ORGANISM: Escherichia coli

<400> SEQUENCE: 27
agccaggccc ataccagcca tactgcggac catttaccat g                41

<210> SEQ ID NO 28
<211> LENGTH: 41
<212> TYPE: DNA
<213> ORGANISM: Escherichia coli

<400> SEQUENCE: 28
agccaggccc ataccagcct ttctgcggac catttaccat g                41

-continued

```
<210> SEQ ID NO 29
<211> LENGTH: 41
<212> TYPE: DNA
<213> ORGANISM: Escherichia coli

<400> SEQUENCE: 29
agccaggccc ataccagccc ctctgcggac catttaccat g          41

<210> SEQ ID NO 30
<211> LENGTH: 40
<212> TYPE: DNA
<213> ORGANISM: Escherichia coli

<400> SEQUENCE: 30
cacaccatta tgaccaaaag acagcccagg ataggcaaat            40

<210> SEQ ID NO 31
<211> LENGTH: 40
<212> TYPE: DNA
<213> ORGANISM: Escherichia coli

<400> SEQUENCE: 31
cacaccatta tgaccaaaag tcagcccagg ataggcaaat            40

<210> SEQ ID NO 32
<211> LENGTH: 39
<212> TYPE: DNA
<213> ORGANISM: Escherichia coli

<400> SEQUENCE: 32
gcgaaacaag cactggacct tcaaactggt actatgctg             39

<210> SEQ ID NO 33
<211> LENGTH: 41
<212> TYPE: DNA
<213> ORGANISM: Escherichia coli

<400> SEQUENCE: 33
agccaggccc ataccagcca atctgcggac catttaccat g          41

<210> SEQ ID NO 34
<211> LENGTH: 41
<212> TYPE: DNA
<213> ORGANISM: Escherichia coli

<400> SEQUENCE: 34
agccaggccc ataccagcca gtctgcggac catttaccat g          41

<210> SEQ ID NO 35
<211> LENGTH: 41
<212> TYPE: DNA
<213> ORGANISM: Escherichia coli

<400> SEQUENCE: 35
agccaggccc ataccagcct tgctgcggac catttaccat g          41

<210> SEQ ID NO 36
<211> LENGTH: 41
<212> TYPE: DNA
<213> ORGANISM: Escherichia coli

<400> SEQUENCE: 36
agccaggccc ataccagcca ttctgcggac catttaccat g          41
```

```
<210> SEQ ID NO 37
<211> LENGTH: 41
<212> TYPE: DNA
<213> ORGANISM: Escherichia coli

<400> SEQUENCE: 37
agccaggccc ataccagcct tcctgcggac catttaccat g                          41

<210> SEQ ID NO 38
<211> LENGTH: 41
<212> TYPE: DNA
<213> ORGANISM: Escherichia coli

<400> SEQUENCE: 38
agccaggccc ataccagccc cactgcggac catttaccat g                          41
```